United States Patent [19]

Edwards et al.

[11] Patent Number: 5,306,619
[45] Date of Patent: Apr. 26, 1994

[54] SCREENING ASSAY FOR THE DETECTION OF DNA-BINDING MOLECULES

[75] Inventors: Cynthia A. Edwards, Menlo Park; Charles R. Cantor, Berkeley, both of Calif.; Beth M. Andrews, Watertown, Mass.

[73] Assignee: Genelabs Technologies, Inc., Redwood City, Calif.

[21] Appl. No.: 81,070

[22] Filed: Jun. 22, 1993

Related U.S. Application Data

[63] Continuation of Ser. No. 723,618, Jun. 27, 1991, abandoned.

[51] Int. Cl.$^5$ .................. C12Q 1/68; C12Q 1/00; G01N 33/566; C07H 17/00
[52] U.S. Cl. ............................ 435/6; 435/172.1; 435/172.3; 435/7.21; 435/7.23; 435/235.1; 436/501; 536/23.1; 536/23.4; 536/23.5; 536/23.6; 536/23.7
[58] Field of Search ............... 435/6, 29, 172.1, 172.3, 435/69.7, 69.1, 7.21, 7.23, 235, 320.1, 340.1; 436/501; 536/23.1, 23.2, 23.51, 23.4, 23.5

[56] References Cited

U.S. PATENT DOCUMENTS

| | | |
|---|---|---|
| 4,257,774 | 3/1981 | Richardson et al. |
| 4,270,924 | 6/1981 | Crooke et al. |
| 5,071,773 | 12/1991 | Evans et al. ............ 436/501 |
| 5,096,815 | 3/1992 | Ladner et al. ........... 435/69.1 |

FOREIGN PATENT DOCUMENTS

WO87/04170 7/1987 PCT Int'l Appl.

OTHER PUBLICATIONS

Davison et al. (1986) J. Gen. Virol. vol. 67, pp. 1759–1816.
McGeoch et al. (1988) J. Gen. Virol. vol. 69, pp. 1531–1574.
Hanvey, J. C., et al., "Site-Specific inhibition of EcoRI restriction/modification enzymes by a DNA triple helix," Nucleic Acids Res. 18(1):157–161 (1990).
Hobson, K., et al., "Use of DNA–Protein Interaction to Isolate Specific Genomic DNA Sequences," Anal. Biochem. 193:220–224 (1991).

Primary Examiner—Robert J. Hill, Jr.
Assistant Examiner—Gian P. Wang
Attorney, Agent, or Firm—Gary R. Fabian; Peter J. Dehlinger

[57] ABSTRACT

The present invention defines a DNA:protein-binding assay useful for screening libraries of synthetic or biological compounds for their ability to bind DNA test sequences. The assay is versatile in that any number of test sequences can be tested by placing the test sequence adjacent to a defined protein binding screening sequence. Binding of molecules to these test sequence changes the binding characteristics of the protein molecule to its cognate binding sequence. When such a molecule binds the test sequence the equilibrium of the DNA:protein complexes is disturbed, generating changes in the concentration of free DNA probe. Also described herein is a method to capture DNA that has been released from the DNA:protein complex.

17 Claims, 14 Drawing Sheets

|  | Test Sequence: | Screening Sequence: | Test Sequence |
|---|---|---|---|

```
UL9Z1     5'-GCGCGCGCGCGTTCGCACTTCCGCCGCCGG-3'
             Z-DNA

UL9Z2     5'-GGCGCCGGCCGTTCGCACTTCGCGCGCGCG-3'
                                    Z-DNA

UL9 CCCG  5'-GGCCCGCCCCGTTCGCACTTCCCGCCCCGG-3'

UL9 GGGC  5'-GGCGGGCGCCGTTCGCACTTGGGCGGGCGG-3'

UL9 ATAT  5'-GGATATATACGTTCGCACTTTAATTATTGG-3'

UL9 polyA 5'-GGAAAAAAACGTTCGCACTTAAAAAAAAGG-3'

UL9 polyT 5'-GGTTTTTTTCGTTCGCACTTTTTTTTTTGG-3'

UL9 GCAC  5'-GGACGCACGCGTTCGCACTTGCAGCAGCGG-3'

ATori-1   5'-GCGTATATATCGTTCGCACTTCGTCCCAAT-3' oriEco2   5'-GGCGAATTCGACGTTCGCACTTCGTCCCAAT-3' oriEco3   5'-GGCGAATTCGATCGTTCGCACTTCGTCCCAAT-3'
```

Fig. 5

| kD | MARKER | GST-UL9 | GST-UL9 +THROMBIN |
|---|---|---|---|
| 97.4 > | | | |
| 69.0 > | | | |
| | |  | |
| 46.0 > | | | |
| 30.0 > | | |  |
| 21.5 > | | | |
Fig. 8

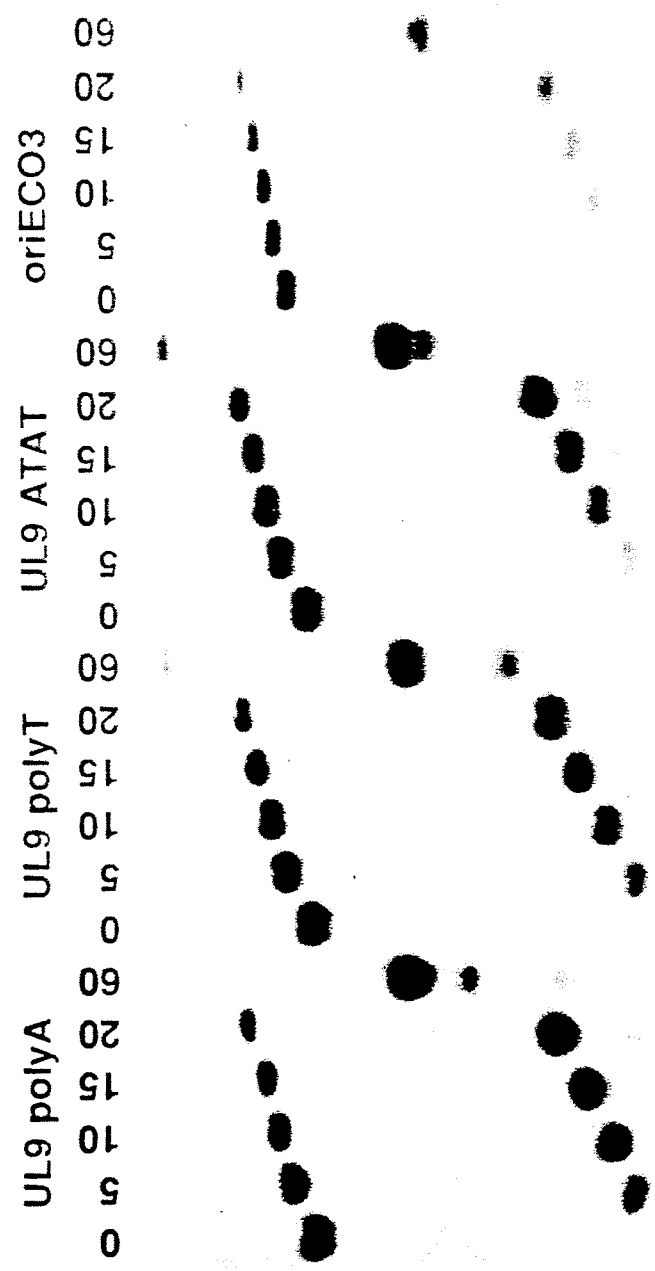
Fig. 9 (con't)

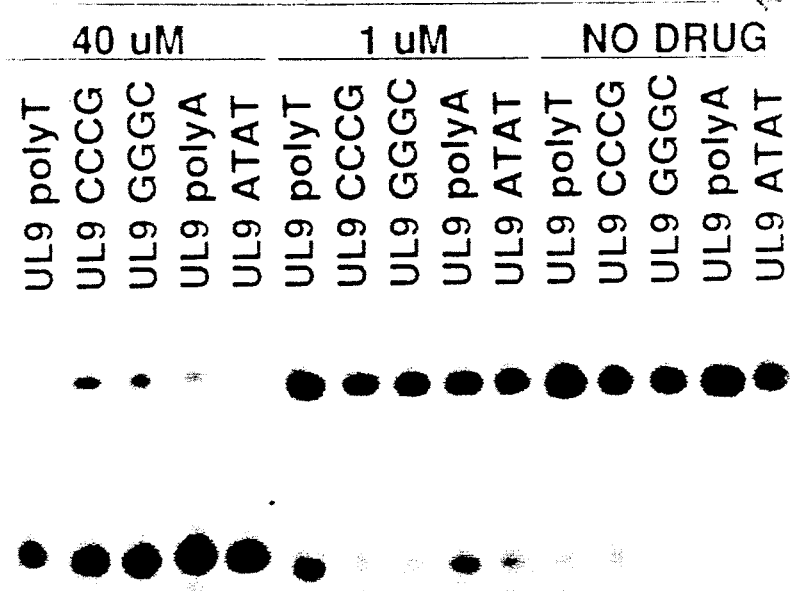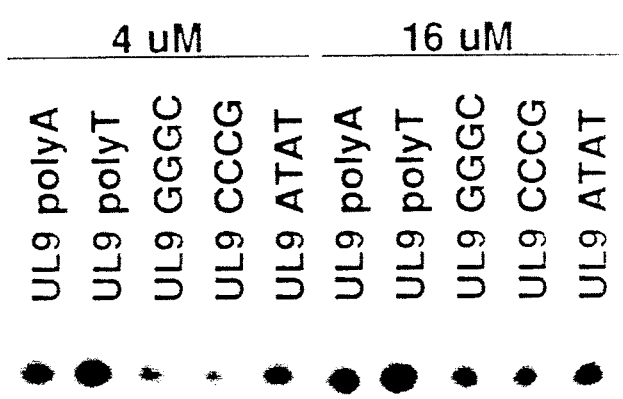
Fig. 10A

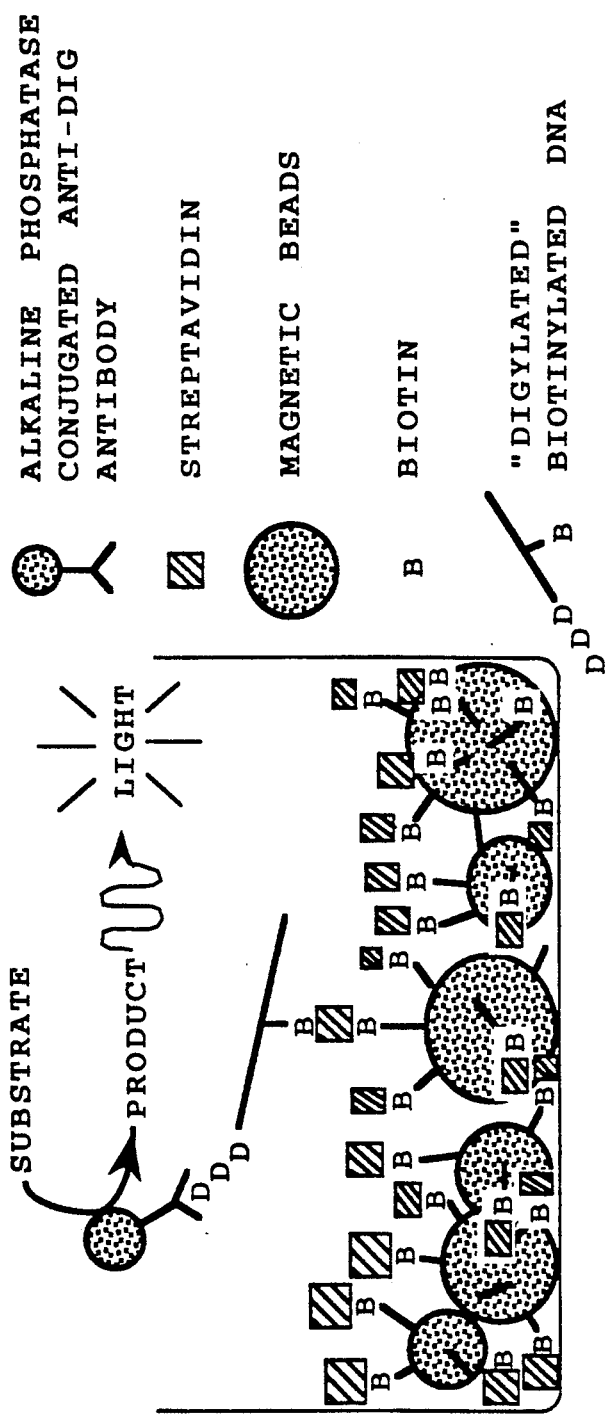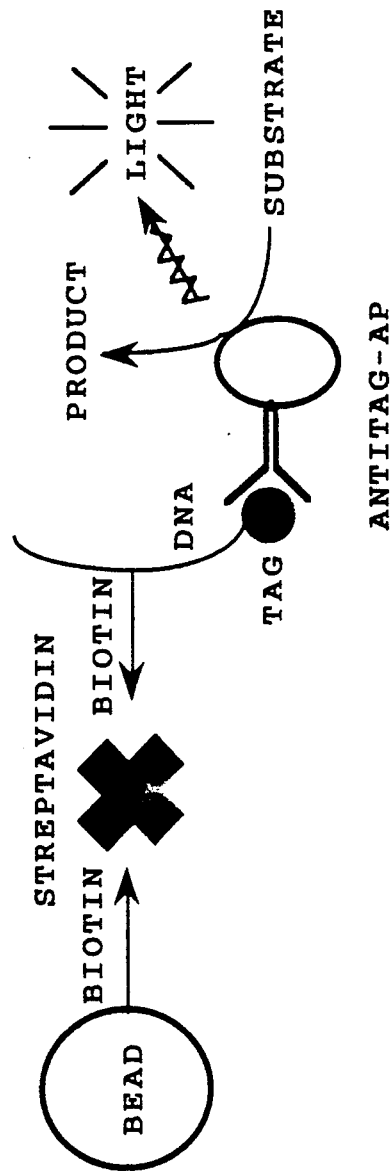
FIG. 11A
FIG. 11B

Table II. Demonstration Assay Test Matrix

| Sequence | \_1 | \_2 | \_3 | \_4 | \_5 | \_6 | \_7 | \_8 |
|---|---|---|---|---|---|---|---|---|
| AGCTTTCGCACTTAGCT | + | – | – | – | – | – | – | – |
| AGCATTCGCACTTAGCA | – | + | – | – | – | – | – | – |
| AGCCTTCGCACTTAGCC | + | – | – | – | – | – | – | + |
| AGCGTTCGCACTTAGCG | + | – | – | – | – | – | – | – |
| TGCTTTCGCACTTTGCT | + | – | – | – | – | – | + | – |
| TGCATTCGCACTTTGCA | + | – | – | + | + | – | + | – |
| TGCCTTCGCACTTTGCC | + | – | – | – | – | – | + | + |
| TGCGTTCGCACTTTGCG | + | – | – | – | – | – | + | – |
| ... | .. | .. | .. | .. | .. | .. | .. | .. |
| ... | .. | .. | .. | .. | .. | .. | .. | .. |
| CCATTTCGCACTTCCAT | + | – | – | + | – | – | – | + |
| CCCTTTCGCACTTCCCT | + | – | – | – | – | – | + | + |
| CCGTTTCGCACTTCCGT | + | – | – | – | – | – | – | + |
| CCTTTTCGCACTTCCTT | + | – | – | – | – | – | + | + |
| ... | .. | .. | .. | .. | .. | .. | .. | .. |

Test Mixtures

Fig. 12

SCREENING ASSAY FOR THE DETECTION OF DNA-BINDING MOLECULES

This is a continuation of application Ser. No. 07/723,618, filed Jun. 27, 1991, now abandoned herein incorporated by reference.

FIELD OF THE INVENTION

The present invention relates to a method, a system, and a kit useful for the identification of molecules that specifically bind to defined nucleic acid sequences.

REFERENCES

Ausubel, F. M., et al., *Current Protocols in Molecular Biology*. John Wiley and Sons, Inc., Media Pa.
Chang, H.-K., et al., Mol. Cell. Biol. November: 5189–5197 (1989).
Chaiet, L., et al., Arch. Biochem. Biophys. 106:1 (1964).
Chen, K-X., et al., J. Biomol. Struct. Dyn. 3:445–466 (1985).
Courtois, G., et al., Proc. Natl. Acad. Sci. USA 85:7937–7941 (1988).
Elias, P., et al., Proc. Natl. Acad. Sci. USA 85:2959–2963 (1988).
Fried, M. G., et al., Nuc. Acid. Res. 9:6505 (1981).
Galas, D., et al., Nuc. Acid. Res. 5:3157–3170 (1981).
Garner, M. M., et al., Nuc. Acid. Res. 9;3047(1981).
Gessner, R. V., et al., Biochemistry 24:237–240 (1985).
Gilbert, D. F., et al., Proc. Natl. Acad. Sci. USA 86:3006 (1988).
Gilman, A. G., et al., eds., *The pharmacologically Basis of Therapeutics*, Eighth Edition, Pergamon Press (1990).
Goldin, A. L., et al., J. Virol. 38:5–58 (1981).
Green, N. M., Adv. Protein Chem. 29:85 (1975).
Harlow, E., et al., *Antibodies: A Laboratory Manual.* Cold Spring Harbor Laboratory Press (1988).
Jain, S. C., et al., J. Mol. Biol. 68:1–20 (1972).
Kadonaga, J. T., PNAS 83:5889–5893 (1986).
Koff, A., et al., J. Virol. 62:4096–4103 (1988).
Luck, G., et al., Nucl. Acids Res. 1:503 (1974).
Luckow, V. A., et al., Virology 170:31 (1989).
Maniatis, T., et al. *Molecular Cloning: A Laboratory Manual,* Cold Spring Harbor Laboratory (1982).
McGeoch, D. J., et al., J. Virology 62(2):444 (1988).
Olivo, P. D., et al., Proc. Natl. Acad. Sci. USA 85:5414–5418 (1988).
Olivo, P. D., et al., J. Virology 3:196–204 (1989).
Polinksy, B., et al., PNAS 72:3310–4 (1975).
Quigley, G. J., et al., Science 232:1255–1258 (1986).
Sambrook, J., et al., In *Molecular Cloning: A Laboratory Manual.* Cold Spring Harbor Laboratory Press, Vol. 2 (1989).
Sherman, S. E., et al., Chem. Rev. 87:1153 (1987).
Siebenlist, U., et al., Proc. Natl. Acad. Sci. USA 77:122–126 (1980).
Smith, D. B., et al., Gene 67:31 (1988).
Sobell, H. M., et al., J. Mol. Biol. 68:21–34 (1972).
Sobell, H. M., Prof. Nucl. Acid. Res. Mol. Biol. 13:153–190 (1973).
Stow, N. D., et al., Virology 130:427–438 (1983).
Summers, M. D., et al., *A manual of Methods for Baculovirus Vectors and Insect Cell Culture Procedures,* Texas Agricultural Experimental Station Bulletin, No. 1555 (1987).
Tullius, T. D., Ann. Rev. Biophys. Biochem. 18:213–237 (1989).
Wartel, R. M., et al., J. Biol. Chem. 15:285–318 (1975).
Weir, H. M., et al., Nucl. Acids Res. 17:1409–1425 (1989).
Woodbury, C. P., et al., Biochemistry 22(20):4730–4737 (1983).
Wu C. A., et al., J. Virol. 62:435–443 (1988).
Zein, N., et al., Science 240:1198 (1988).
Zimmer, C., Pros. Nucl. Acid Res. Mol. Biol. 15:285–318 (1975).

BACKGROUND OF THE INVENTION

Several classes of small molecules that interact with double-stranded DNA have been identified. Many of these small molecules have profound biological effects. For example, many aminoacridines and polycyclic hydrocarbons bind DNA and are mutagenic, teratogenic, or carcinogenic. Other small molecules that bind DNA include: biological metabolites, some of which have applications as antibiotics and antitumor agents including actinomycin D, echinomycin, distamycin, and calicheamicin; planar dyes, such as ethidium and acridine orange; and molecules that contain heavy metals, such as cisplatin, a potent antitumor drug.

Most known DNA-binding molecules do not have a known sequence binding preference. However, there are a few small DNA-binding molecules that preferentially recognize specific nucleotide sequences, for example: echinomycin preferentially binds the sequence [(A/T)CGT]/[ACG(A/T)] (Gilbert et al.); cisplatin covalently cross-links a platinum molecule between the N7 atoms of two adjacent deoxyguanosines (Sherman et al.); and calicheamicin preferentially binds and cleaves the sequence TCCT/AGGA (Zein et al.).

The biological response elicited by most therapeutic DNA-binding molecules is toxicity, specific only in that these molecules may preferentially affect cells that are more actively replicating or transcribing DNA than other cells. Targeting specific sites may significantly decrease toxicity simply by reducing the number of potential binding sites in the DNA. As specificity for longer sequences is acquired, the nonspecific toxic effects due to DNA-binding may decrease. Many therapeutic DNA-binding molecules initially identified based on their therapeutic activity in a biological screen have been later determined to bind DNA.

Experiments performed in support of the present invention have identified an in vitro assay useful to screen for DNA-binding molecules. The assay also allows the discrimination of sequence binding preferences of such molecules. The potential therapeutic applications for molecules that bind to specific DNA sequences are widespread.

SUMMARY OF THE INVENTION

The present invention provides a method for screening molecules or compounds capable of binding to a selected test sequence in a duplex DNA. The method involves adding a molecule to be screened, or a mixture containing the molecule, to a test system. The test system includes a DNA binding protein that is effective to bind to a screening sequence, i.e. the DNA binding protein's cognate binding site, in a duplex DNA with a binding affinity that is substantially independent of the sequences adjacent the binding sequence—these adjacent sequences are referred to as test sequences. But, the DNA binding protein is sensitive to binding of molecules to such test sequence, when the test sequence is adjacent the screening sequence. The test system further includes a duplex DNA having the screening and test sequences adjacent one another. Also, the binding protein is present in an amount that saturates the screening sequence in the duplex DNA. The molecule is incubated in contact with the test system for a period sufficient to permit binding of the molecule being tested to the test sequence in the duplex DNA. The amount of binding protein bound to the duplex DNA is compared before and after the addition of the test molecule or mixture.

Candidates for the screening sequence/binding protein may be selected from the following group: EBV origin of replication/EBNA, HSV origin of replication/UL9, VZV origin of replication/UL9-like, HPV origin of replication/E2, interleukin 2 enhancer/NFAT-1, HIV-LTR/NFAT-1, HIV-LTR/NFkB, HBV enhancer/HNF-1, fibrinogen promoter/HNF-1, lambda $o_L$-$o_R$/cro, and other known DNA:protein interactions.

A preferred embodiment of the present invention utilizes the UL9 protein, or DNA-binding proteins derived therefrom, and its cognate binding sequence SEQ ID NO:1, SEQ ID NO:2, or SEQ ID NO:15.

The test sequences can be any combination of sequences of interest. The sequences may be randomly generated for shot-gun approach screening or specific sequences may be chosen. Some specific sequences of medical interest include the following sequences involved in DNA:protein interactions: EBV origin of replication, HSV origin of replication, VZV origin of replication, HPV origin of replication, interleukin 2 enhancer, HIV-LTR, HBV enhancer, and fibrinogen promoter.

In the above method, comparison of protein-bound to free DNA can be accomplished using either a gel bandshift assay, a filter-binding assay, or a capture/detection assay.

In one embodiment of the DNA capture/detection assay the capture system involves the biotinylation of a nucleotide within the screening sequence (i) that does not eliminate the protein's ability to bind to the screening sequence, (ii) that is capable of binding streptavidin, and (iii) where the biotin moiety is protected from interactions with streptavidin when the protein is bound to the screening sequence. The capture/detection assay also involves the detection of the captured DNA.

The present invention also includes a screening system for identifying molecules that are capable of binding to a test sequence in a duplex DNA sequence. The system includes a DNA binding protein that is effective to bind to a screening sequence in a duplex DNA with a binding affinity that is substantially independent of a test sequence adjacent the screening sequence. The binding of the DNA protein is, however, sensitive to binding of molecules to the test sequence when the test sequence is adjacent the screening sequence. The system includes a duplex DNA having the screening and test sequences adjacent one another. Typically, the binding protein is present in an amount that saturates the screening sequence in the duplex DNA. The system also includes means for detecting the amount of binding protein bound to the DNA.

As described above the test sequences can be any number of sequences of interest.

The screening sequence/binding protein can be selected from known DNA:protein interactions using the criteria and guidance of the present disclosure.

A preferred embodiment of the screening system of the present invention includes the UL9 protein, or DNA-binding protein derived therefrom (e.g., the truncated UL9 protein designated UL9-COOH). In this embodiment the duplex DNA has (i) a screening sequence selected from the group consisting of SEQ ID NO:1, SEQ ID NO:2, and SEQ ID NO:15, and (ii) a test sequence adjacent the screening sequence, where UL9 is present in an amount that saturates the screening sequence. The system further includes means for detecting the amount of UL9 bound to the DNA, including, band-shift assays, filter-binding assays, and capture/detection assays.

The present disclosure describes the procedures needed to test DNA:protein interactions for their suitability for use in the screening assay of the present invention.

The present invention further defines a DNA capture system and detection system. In the first part of this system, the cognate DNA binding site of the DNA binding protein is modified with a detection moiety, such as biotin or digoxigenin. The modification must be made to the site in such a manner that (i) it does not eliminate the protein's ability to bind to the cognate binding sequence, (ii) the moiety is accessible to the capturing agent (e.g., in the case of biotin the agent is streptavidin) in DNA that is not bound to protein, and (iii) where the moiety is protected from interactions with the capture agent when the protein is bound to the screening sequence.

In the second part of this system, the target oligonucleotide is labelled to allow detection. Labelling of the target oligonucleotide can be accomplished by standard techniques such as radiolabelling. Alternatively, a moiety such as digoxigenin can be incorporated in the target oligonucleotide and this moiety can then be detected after capture.

Two embodiments of the capture/detection system described by the present disclosure are as follows:

(i) the target oligonucleotide (containing, for example, the screening and test sequences)—modification of the cognate binding site with biotin and incorporation of digoxigenin; capture of the target oligonucleotide using streptavidin attached to a solid support; and detection of the target oligonucleotide using a tagged anti-digoxigenin antibody.

(ii) the target oligonucleotide—modification of the cognate binding site with digoxigenin and incorporation of biotin; capture of the target oligonucleotide using an anti-digoxigenin antibody attached to a solid support; and detection of the target oligonucleotide using tagged streptavidin.

BRIEF DESCRIPTION OF THE FIGURES

FIG. 5 shows a series of sequences that have been tested in the assay of the present invention for the binding of sequence-specific small molecules.

FIG. 8 is a photograph of a SDS-polyacrylamide gel showing (i) the purified UL9-COOH/glutathione-S-transferase fusion protein and (ii) the UL9-COOH polypeptide.

FIG. 10A shows the effect of the addition of several concentrations of Distamycin A to DNA:protein assay reactions utilizing different test sequences.

FIG. 11A illustrates a DNA capture system of the present invention utilizing biotin and streptavidin coated magnetic beads. The presence of the DNA is detected using an alkaline-phosphatase substrate that yields a chemiluminescent product. FIG. 11B shows a similar reaction using biotin coated agarose beads that are conjugated to streptavidin, that in turn is conjugated to the captured DNA.

FIG. 12 demonstrates a test matrix based on DNA:-protein-binding data.

DETAILED DESCRIPTION OF THE INVENTION

Definitions

Figure 1:
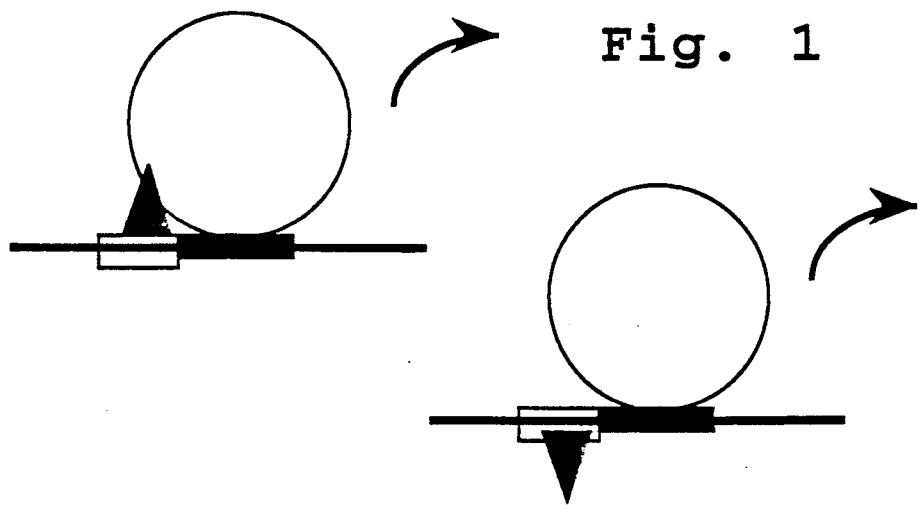
FIG. 1A illustrates how a DNA-binding protein is displaced by a small molecule because of steric hinderance.
FIG. 1B illustrates how a DNA-binding protein is displaced because of conformational changes induced in the DNA by a small molecule.

Small molecules are desirable as therapeutics for several reasons related to drug delivery: (i) they are commonly less than 10 K molecular weight; (ii) they are more likely to be permeable to cells; (iii) unlike peptides or oligonucleotides, they are less susceptible to degradation by many cellular mechanisms; and, (iv) they are not as apt to elicit an immune response. Many pharmaceutical companies have extensive libraries of chemical and/or biological mixtures, often fungal, bacterial, or algal extracts, that would be desirable to screen with the assay of the present invention. Small molecules may be either biological or synthetic organic compounds, or even inorganic compounds (i.e., cisplatin).

Dissociation is the process by which two molecules cease to interact: the process occurs at a fixed average rate under specific physical conditions.

Functional binding is the noncovalent association of a protein or small molecule to the DNA molecule. In the assay of the present invention the functional binding of the protein to the screening sequence (i.e., its cognate DNA binding site) has been evaluated using filter binding or gel band-shift experiments.

On-rate is herein defined as the time required for two molecules to reach steady state association: for example, the DNA:protein complex.

Off-rate is herein defined as the time required for one-half of the associated complexes, e.g., DNA:protein complexes, to dissociate.

Sequence-specific binding refers to DNA binding molecules which have a strong DNA sequence binding preference. For example, restriction enzymes and the proteins listed in Table I demonstrate typical sequence-specific DNA-binding.

Sequence-preferential binding refers to DNA binding molecules that generally bind DNA but that show preference for binding to some DNA sequences over others. Sequence-preferential binding is typified by several of the small molecules tested in the present disclosure, e.g., distamycin. Sequence-preferential and sequence-specific binding can be evaluated using a test matrix such as is presented in FIG. 12.

Screening sequence is the DNA sequence that defines the cognate binding site for the DNA binding protein: in the case of UL9 the screening sequence can, for example, be SEQ ID NO:1.

Test sequence is a DNA sequence adjacent the screening sequence. The assay of the present invention screens for molecules that, when bound to the test sequence, affect the interaction of the DNA-binding protein with its cognate binding site (i.e., the screening sequence). Test sequences can be placed adjacent either or both ends of the screening sequence. Typically binding of molecules to the test sequence interfere with the binding of the DNA-binding protein to the screening sequence. However, some molecules binding to these sequences may have the reverse effect, causing an increased binding affinity of the DNA-binding protein to the screening sequence.

I. The Assay

One feature of the present invention is that it provides an assay to screen libraries of synthetic or biological compounds, including small molecules and proteins, for their ability to bind DNA in a sequence-preferential manner.

A. General Considerations

The assay of the present invention has been designed for detecting test molecules or compounds that affect the rate of transfer of a specific DNA molecule from one protein molecule to another identical protein in solution.

A mixture of DNA and protein is prepared in solution. The concentration of protein is in excess to the concentration of the DNA so that virtually all of the DNA is found in DNA:protein complexes. The DNA is a double-stranded oligonucleotide that contains the recognition sequence for a specific DNA-binding protein (i.e., the screening sequence). The protein used in the assay contains a DNA-binding domain that is specific for binding to the sequence within the oligonucleotide. The physical conditions of the solution (e.g., pH, salt concentration, temperature) are adjusted such that the half-life of the complex is amenable to performing the assay (optimally a half-life of 5–30 minutes).

As one DNA:protein complex dissociates, the released DNA rapidly reforms a complex with another protein in solution. Since the protein is in excess to the DNA, dissociations of one complex always result in the rapid reassociation of the DNA into another DNA:protein complex. At equilibrium, very few DNA molecules will be unbound. The minimum background of the assay is the amount of unbound DNA observed during any given measurable time period. The brevity of the observation period and the sensitivity of the detection system define the lower limits of background DNA.

FIG. 1A illustrates how such a protein can be displaced from its cognate binding site by steric hinderance of a small molecule. Alternatively, a molecule may interfere with a DNA:protein binding interaction by inducing a conformational change in the DNA (FIG. 1B). In either event, if a test molecule that binds the oligonucleotide hinders binding of the protein, the rate of transfer of DNA from one protein to another will be decreased. This will result in a net increase in the amount of unbound DNA. In other words, an increase in the amount of unbound DNA indicates the presence of an inhibitor.

Alternatively, molecules may be isolated that, when bound to the DNA, cause an increased affinity of the DNA-binding protein for its cognate binding site. In this case the amount of unbound DNA (observed during a given measurable time period after the addition of the molecule) will decrease in the reaction mixture as detected by the capture/detection system described in Section II.

B. Choosing a DNA:protein Complex

There are several approaches that could be taken to look for small molecules that specifically inhibit the interaction of a given DNA-binding protein with its binding sequence (cognate site). One approach would be to test biological or chemical compounds for their ability to preferentially block the binding of one specific DNA:protein interaction but not the others. Such an assay would depend on the development of at least two, preferably three, DNA:protein interaction systems in order to establish controls for distinguishing between general DNA-binding molecules (polycations like heparin or intercalating agents like ethidium) and DNA-binding molecules having sequence binding preferences that would affect protein/cognate binding site interactions in one system but not the other(s).

One illustration of how this system could be used is as follows. Each cognate site could be placed 5' to a reporter gene (such as genes encoding β-galactoside or luciferase) such that binding of the protein to the cognate site would block transcription of the reporter gene. In the case where multiple protein/cognate binding sites are used for screening, a competitive inhibitor that blocks one interaction but not the others could be identified by the lack of transcription of a reporter gene in a transfected cell line or in an in vitro assay. Only one such DNA-binding sequence, specific for the protein of interest, could be screened with each assay system. This approach has a number of limitations including limited testing capability and the need to construct the appropriate reporter system for each different protein/cognate site of interest.

Experiments performed in support of the present invention have defined a second approach for identifying molecules having sequence-preferential DNA-binding. In this approach small molecules binding to sequences adjacent the cognate binding sequence can inhibit the protein/cognate DNA interaction. This assay has been designed to use a single DNA:protein interaction to screen for sequence-specific or sequence-preferential DNA-binding molecules that recognize virtually any sequence.

While DNA-binding recognition sites are usually quite small (4-17 bp), the sequence that is protected by the binding protein is larger (usually 5 bp or more on either side of the recognition sequence—as detected by DNAase I protection (Galas et al.) or methylation interference (Siebenlist et al.). Experiments performed in support of the present invention demonstrated that a single protein and its cognate DNA-binding sequence can be used to assay virtually any DNA sequence by placing a sequence of interest adjacent to the cognate site: a small molecule bound to the adjacent site can be detected by the dissociation of the protein from its cognate site. Such dissociation might occur by either steric hindrance or induced conformational changes in the recognition sequence for the protein.

There are several considerations involved in choosing DNA:protein complexes that can be employed in the assay of the present invention including:

The off-rate (i.e., the time period from contact of the protein with the DNA site until disassociation) should be fast enough to accomplish the assay in a reasonable amount of time. The interactions of some proteins with cognate sites in DNA can be measured in days not minutes: such tightly bound complexes would inconveniently lengthen the period of time it takes to perform the assay.

2) The off-rate should be slow enough to allow the measurement of unbound DNA in a reasonable amount of time. The level of background free DNA is dictated by the ratio between the time needed to measure free DNA and the amount of free DNA that occurs naturally due to the off-rate during the measurement time period.

In view of the above two considerations, practical useful DNA:protein off-rates fall in the range of approximately two minutes to several days.

3) A further consideration is that the kinetic interactions of the DNA:protein complex is insensitive to the nucleotide sequences flanking the recognition sequence. The affinity of many DNA-binding proteins is affected by differences in the sequences adjacent to the recognition sequence. The most obvious example of this phenomenon is the preferential binding and cleavage of restriction enzymes given a choice of several identical recognition sequences with different flanking sequences (Polinsky et al.). If the off-rates are affected by flanking sequences the analysis of comparative binding data between different flanking oligonucleotide sequences becomes difficult but is not impossible.

Experiments performed in support of the present invention have identified a DNA:protein interaction that is particularly useful for the above described assay: the Herpes Simplex Virus (HSV) UL9 protein that binds the HSV origin of replication (oriS). The UL9 protein has fairly stringent sequence specificity. There appear to be two binding sites for UL9 in oriS, SEQ ID NO:1 and SEQ ID NO:2 (Stow et al.). One sequence (SEQ ID NO:1) binds with at least 10-fold higher affinity than the second sequence (SEQ ID NO:2): the embodiments described below use the higher affinity binding site (SEQ ID NO:1).

DNA:protein association reactions are performed in solution. The DNA:protein complexes can be separated from free probe by any of several methods. One particularly useful method for the initial study of DNA:protein interactions has been visualization of binding results using band shift gels (Example 3A). In this method DNA:protein binding reactions containing both labelled complexes and free DNA are separated electrophoretically on polyacrylamide/TBE gels. These gels are fixed, dried, and exposed to X-ray film. The resulting autoradiograms are examined for the amount of free probe that is migrating separately from the DNA:-protein complex. These assays include (i) a lane containing only free labeled probe, and (ii) a lane where the sample is labeled probe in the presence of a large excess of binding protein. The band shift assays allow visualization of the ratios between DNA:protein complexes and free probe. However, they are less accurate than filter binding assays for rate-determining experiments due to the lag time between loading the gel and electrophoretic separation of the components.

The filter binding method is particularly useful in determining the off-rates for protein:oligonucleotide complexes (Example 3B). In the filter binding assay, DNA:protein complexes are retained on a filter while free DNA passes through the filter. This assay method is more accurate for off-rate determinations because the separation of DNA:protein complexes from free probe is very rapid. The disadvantage of filter binding is that the nature of the DNA:protein complex cannot be directly visualized. So if, for example, two proteins are used with a single DNA molecule, filter binding assays cannot differentiate between the binding of the two proteins nor yield information about whether one or both proteins are binding.

There are many known DNA:protein interactions that may be useful in the practice of the present invention, including (i) the DNA protein interactions listed in Table I, (ii) bacterial, yeast, and phage systems such as lambda $o_L$-$o_R$/cro, and (iii) modified restriction enzyme systems (e.g., protein binding in the absence of divalent cations). Any protein that binds to a specific recognition sequence may be useful in the present invention. The major constraining factor is the effect of the immediately adjacent sequences (the test sequences) on the affinity of the protein for its recognition sequence. DNA:protein interactions in which there is little or no effect of the test sequences on the affinity of the protein for its cognate site are preferable for use in the described assay; however, DNA:protein interactions that exhibit (test sequence-dependent) differential binding may still be useful if algorithms are applied to the analysis of data that compensate for the differential affinity. The present disclosure provides methods and guidance for testing the usefulness of such DNA:protein interactions, i.e., other than UL9, in the screening assay.

C. Preparation of Full Length UL9 and UL9-COOH Polypeptides

UL-9 protein has been prepared by a number of recombinant techniques (Example 2). The full length UL9 protein has been prepared from baculovirus infected insect cultures (Example 3A, B, and C). Further, a portion of the UL9 protein that contains the DNA-binding domain (UL9-COOH) has been cloned into a bacterial expression vector and produced by bacterial cells (Example 3D and E). The DNA-binding domain of UL9 is contained within the C-terminal 317 amino acids of the protein (Weir et al.). The UL9-COOH polypeptide was inserted into the expression vector in-frame with the glutathione-S-transferase (gst) protein. The gst/UL9 fusion protein was purified using affinity chomatography (Example 3E). The vector also contained a thrombin cleavage site at the junction of the two polypeptides. Therefore, once the fusion protein was isolated (FIG. 8, lane 2) it was treated with thrombin, cleaving the UL9-COOH/ gst fusion protein from the gst polypeptide (FIG. 8, lane 3). The UL9-COOH-gst fusion polypeptide was obtained at a protein purity of greater than 95% as determined using Coomaisie staining.

Other hybrid proteins can be utilized to prepare DNA-binding proteins of interest. For example, fusing a DNA-binding protein coding sequence in-frame with a sequence encoding the thrombin site and also in-frame with the β-galactoside coding sequence. Such hybrid proteins can be isolated by affinity or immunoaffinity columns (Maniatis et al.; Pierce, Rockford IL). Further, DNA-binding proteins can be isolated by affinity chromatography based on their ability to interact with their cognate DNA binding site. For example, the UL9 DNA-binding site (SEQ ID NO:1) can be covalently linked to a solid support (e.g., CnBr-activated Sepharose 4B beads, Pharmacia, Piscataway N.J.), extracts passed over the support, the support washed, and the DNA-binding then isolated from the support with a salt gradient (Kadonaga).

The results presented below in regard to the DNA-binding ability of the truncated UL9 protein suggest that full length DNA-binding proteins are not required for the DNA:protein assay of the present invention: only a portion of the protein containing the cognate site recognition function may be required. The portion of a DNA-binding protein required for DNA-binding can be evaluated using a functional binding assay (Example 4A). The rate of dissociation can be evaluated (Example 4B) and compared to that of the full length DNA-binding protein.

D. Functional Binding and Rate of Dissociation.

The full length UL9 and purified UL9-COOH proteins were tested for functional activity in "band shift" assays (see Example 4A). The buffer conditions were optimized for DNA:protein-binding (Example 4C) using the UL9-COOH polypeptide. These DNA-binding conditions also worked well for the full-length UL9 protein. Radiolabelled oligonucleotides (SEQ ID NO:14) that contained the 11 bp UL9 DNA-binding recognition sequence (SEQ ID NO:1) were mixed with each UL9 protein in appropriate binding buffer. The reactions were incubated at room temperature for 10 minutes (binding occurs in less than 2 minutes) and the products were separated electrophoretically on nondenaturing polyacrylamide gels (Example 4A). The degree of DNA:protein-binding could be determined from the ratio of labeled probe present in DNA:protein complexes versus that present as free probe. This ratio was typically determined by optical scanning of autoradiograms and comparison of band intensities. Other standard methods may be used as well for this determination, such as scintillation counting of excised bands. The UL9-COOH polypeptide and the full length UL9 polypeptide, in their respective buffer conditions, bound the target oligonucleotide equally well.

The rate of dissociation was determined using competition assays. An excess of unlabelled oligonucleotide that contained the UL9 binding site was added to each reaction. This unlabelled oligonucleotide acts as a specific inhibitor, capturing the UL9 protein as it dissociates from the labelled oligonucleotide (Example 4B). The dissociation rate, as determined by a band-shift assay, for both full length UL9 and UL9-COOH was approximately 4 hours at 4° C. Neither non-specific oligonucleotides (a 10,000-fold excess) nor sheared herring sperm DNA (a 100,000-fold excess) competed for binding with the oligonucleotide containing the UL9 binding site.

E. oriS Flanking Sequence Variation.

As mentioned above, one feature of a DNA:protein-binding system for use in the assay of the present invention is that the DNA:protein interaction is not affected by the nucleotide sequence of the regions adjacent the DNA-binding site. The sensitivity of any DNA:protein-binding reaction to the composition of the flanking sequences can be evaluated by the functional binding assay and dissociation assay described above.

To test the effect of flanking sequence variation on UL9 binding to the oriS SEQ ID NO:1 sequences oligonucleotides were constructed with 20–30 different sequences (i.e., the test sequences) flanking the 5' and 3' sides of the UL9 binding site. Further, oligonucleotides were constructed with point mutations at several positions within the UL9 binding site. Most point mutations within the binding site destroyed recognition. Several changes did not destroy recognition and these include variations at sites that differ between the two UL9 binding sites (SEQ ID NO:1 and SEQ ID NO:2): the second UL9 binding site (SEQ ID NO:2) shows a ten-fold decrease in UL9:DNA binding affinity (Elias et al.) relative to the first (SEQ ID NO:1). On the other hand, sequence variation at the test site (also called the test sequence), adjacent to the screening site (FIG. 5, Example 5), had virtually no effect on binding or the rate of dissociation.

Taken together the above experiments support that the UL9-COOH polypeptide binds the SEQ ID NO:1 sequence with (i) appropriate strength, (ii) an acceptable disassociation time, and (iii) indifference to the nucleotide sequences flanking the assay (binding) site. These features suggested that the UL9/oriS system could provide a versatile assay for detection of small molecule/DNA-binding involving any number of specific nucleotide sequences.

The above-described experiment can be used to screen other DNA:protein interactions to determine their usefulness in the present assay.

F. Small Molecules as Sequence-Specific Competitive Inhibitors

To test the utility of the present assay system several small molecules that have sequence preferences (i.e., a preference for AT-rich versus GC-rich sequences) have been tested.

Distamycin A binds relatively weakly to DNA ($K_A = 2 \times 10^5$ M$^{-1}$) with a preference for non-alternating AT-rich sequences (Jain et al.; Sobell; Sobell et al.). Actinomycin D binds DNA more strongly ($K_A = 7.6 \times 10^{-7}$ M$^{-1}$) than Distamycin A and has a relatively strong preference for the dinucleotide sequence dGdC (Luck et al.; Zimmer; Wartel). Each of these molecules poses a stringent test for the assay. Distamycin A tests the sensitivity of the assay because of its relatively weak binding. Actinomycin D challenges the ability to utilize flanking sequences since the UL9 recognition sequence contains a dGdC dinucleotide: therefore, it might be anticipated that all of the oligonucleotides, regardless of the test sequence flanking the assay site, might be equally affected by actinomycin D.

In addition, Doxorubicin, a known anti-cancer agent that binds DNA in a sequence-preferential manner (Chen, K-X, et al.), has been tested for preferential DNA sequence binding using the assay of the present invention.

Actinomycin D, Distamycin A, and Doxorubicin have been tested for their ability to preferentially inhibit the binding of UL9 to oligonucleotides containing different sequences flanking the UL9 binding site (Example 6, FIG. 5). Binding assays were performed as described in Example 5. These studies were completed under conditions in which UL9 is in excess of the DNA (i.e., most of the DNA is in complex).

Distamycin A was tested with 5 different test sequences flanking the UL9 screening sequence: SEQ ID NO:5 to SEQ ID NO:9. The results shown in FIG. 10A demonstrate that distamycin A preferentially disrupts binding to the test sequences UL9 polyT, UL9 polyA and, to a lesser extent, UL9 ATAT. FIG. 10A also shows the concentration dependence of the inhibitory effect of distamycin A: at 1 μM distamycin A most of the DNA:protein complexes are intact (top band) with free probe appearing in the UL9 polyT and UL9 polyA lanes, and some free probe appearing in the UL9 ATAT lane; at 4 μM free probe can be seen in the UL9 polyT and UL9 polyA lanes; at 16 μM free probe can be seen in the UL9 polyT and UL9 polyA lanes; and at 40 μM the DNA:protein in the polyT, UL9 polyA and UL9 ATAT lanes are near completely disrupted while some DNA:protein complexes in the other lanes persist. These results are consistent with Distamycin A's known binding preference for non-alternating AT-rich sequences.

Actinomycin D was tested with 8 different test sequences flanking the UL9 screening sequence: SEQ ID NO:5 to SEQ ID NO:9, and SEQ ID NO:11 to SEQ ID NO:13. The results shown in FIG. 10B demonstrate that actinomycin D preferentially disrupts the binding of UL9-COH to the oligonucleotides UL9 CCCG (SEQ ID NO:5) and UL9 GGGC (SEQ ID NO:6). These oligonucleotides contain, respectively, three or five dGdC dinucleotides in addition to the dGdC dinucleotide within the UL9 recognition sequence. This result is consistent with Actinomycin D's known binding preference for the dinucleotide sequence dGdC. Apparently the presence of a potential target site within the screening sequence (oriS, SEQ ID NO:1), as mentioned above, does not interfere with the function of the assay.

Figure 10B:
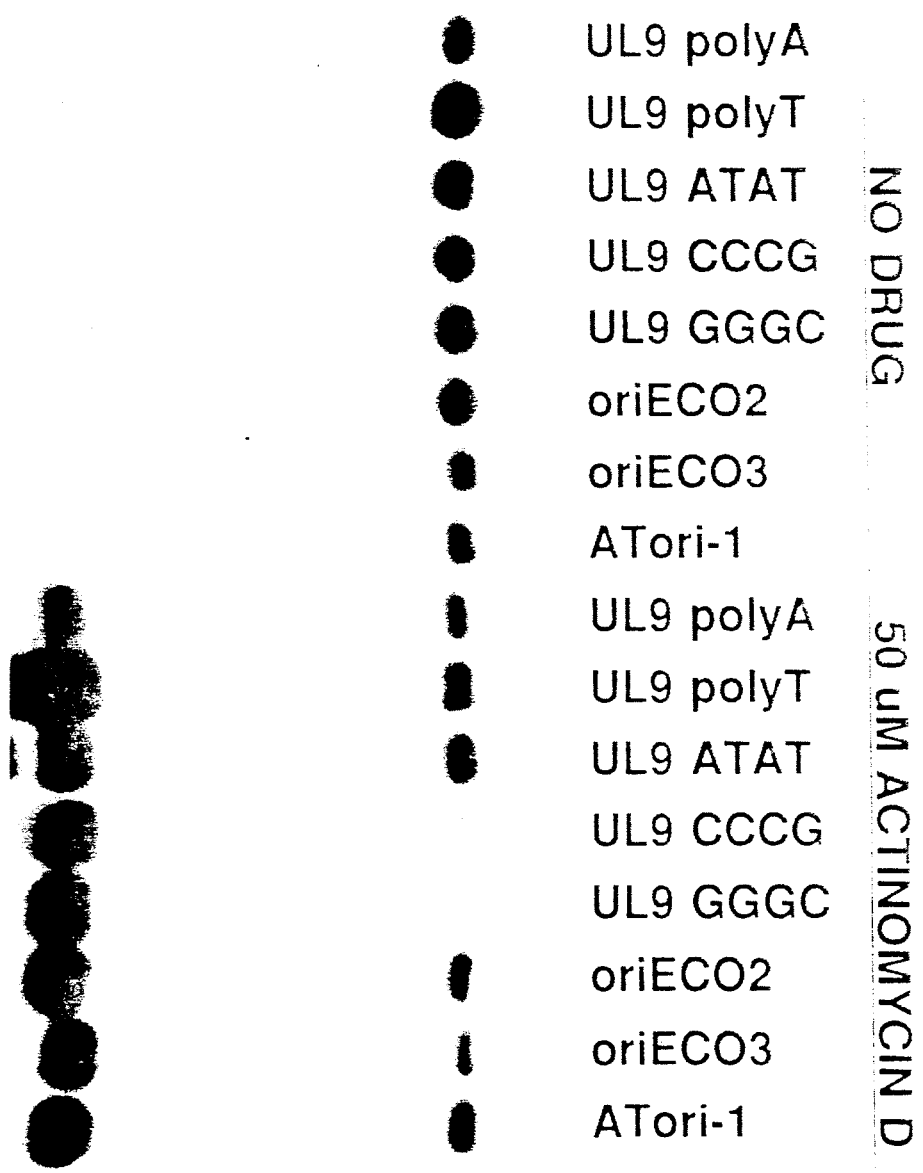
FIG. 10B shows the effect of the addition of Actinomycin D to DNA:protein assay reactions utilizing different test sequences.
Figure 10C:
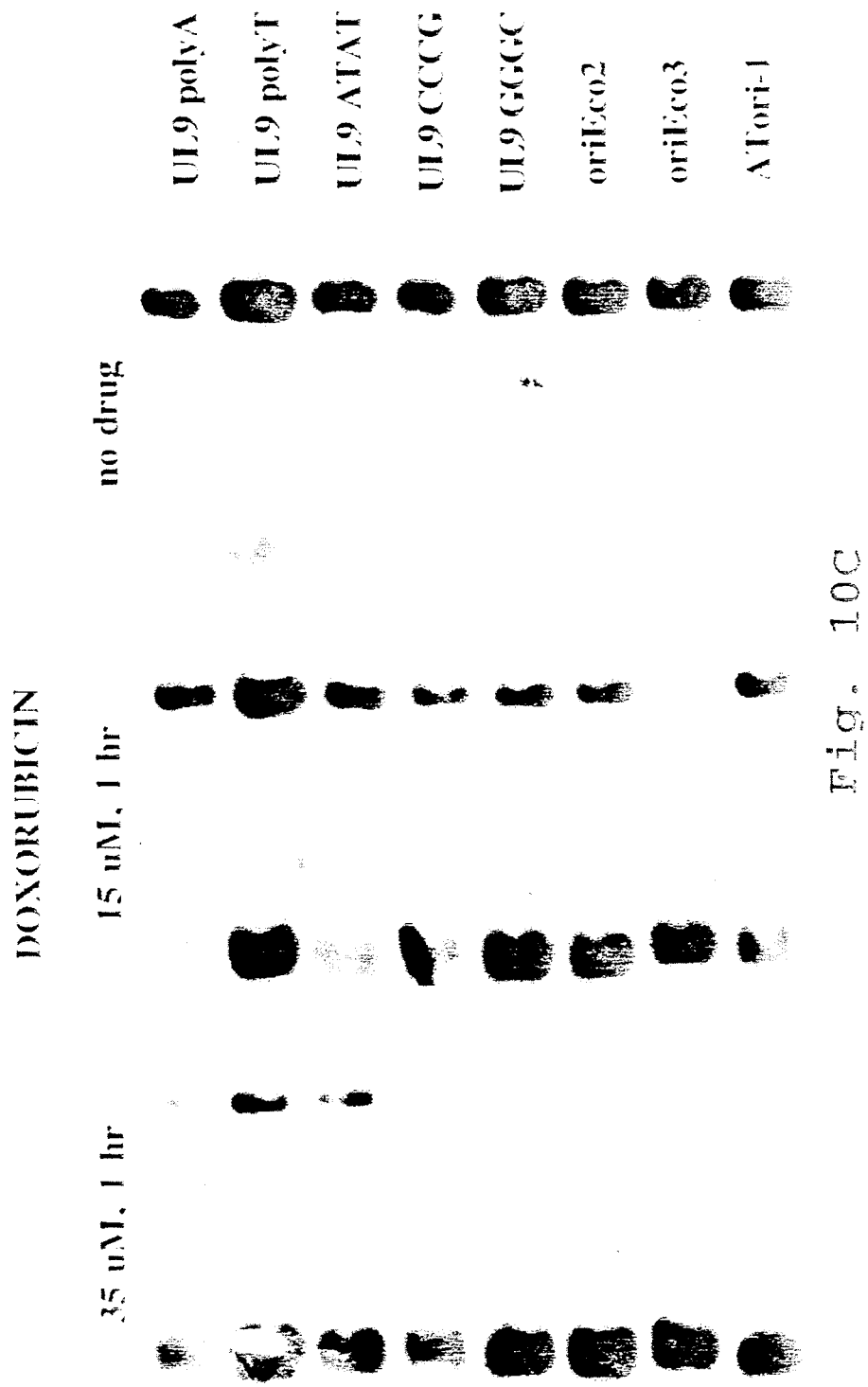
FIG. 10C shows the effect of the addition of Doxorubicin to DNA:protein assay reactions utilizing different test sequences.

Doxorubicin was tested with 8 different test sequences flanking the UL9 screening sequence: SEQ ID NO:5 to SEQ ID NO:9, and SEQ ID NO:11 to SEQ ID NO:13. The results shown in FIG. 10C demonstrate that Doxorubicin preferentially disrupts binding to oriEco3, the test sequence of which differs from oriEco2 by only one base (compare SEQ ID NO:12 and SEQ ID NO:13). FIG. 10C also shows the concentration dependence of the inhibitory effect of Doxorubicin: at 15 μM Doxorubicin, the UL9 binding to the screening sequence is strongly affected when oriEco3 is the test sequence, and more mildly affected when polyT, UL9 GGGC, or oriEco2 was the test sequence; and at 35 μM Doxorubicin most DNA:protein complexes are nearly completely disrupted, with UL9 polyT and UL9ATAT showing some DNA still complexed with protein. Also, effects similar to those observed at 15 μM were also observed using Doxorubicin at 150 nM, but at a later time point.

Further incubation with any of the drugs resulted in additional disruption of binding. Given that the one hour incubation time of the above assays is equivalent to several half-lives of the DNA:protein complex, the additional disruption of binding suggests that the on-rate for the drugs is comparatively slow.

The ability of the assay to distinguish sequence binding preference using weak DNA-binding molecules with poor sequence-specificity (such as distamycin A) is a stringent test. Accordingly, the present assay seems well suited for the identification of molecules having better sequence specificity and/or higher sequence binding affinity. Further, the results demonstrate sequence preferential binding with the known anti-cancer drug Doxorubicin. This result suggests the assay may be useful for screening small molecule mixtures for molecules displaying similar characteristics that could be subsequently tested for anti-cancer activities.

Other compounds that may be suitable for testing the present DNA:protein system or for defining alternate DNA:protein systems include the following: echinomycin, which preferentially binds to the sequence (A/T)CGT (Quigley et al.); and small inorganic molecules, such as cobalt hexamine, that are known to induce Z-DNA formation in regions that contain repetitive GC sequences (Gessner et al.).

II. Capture/Detection Systems

Figure 2:
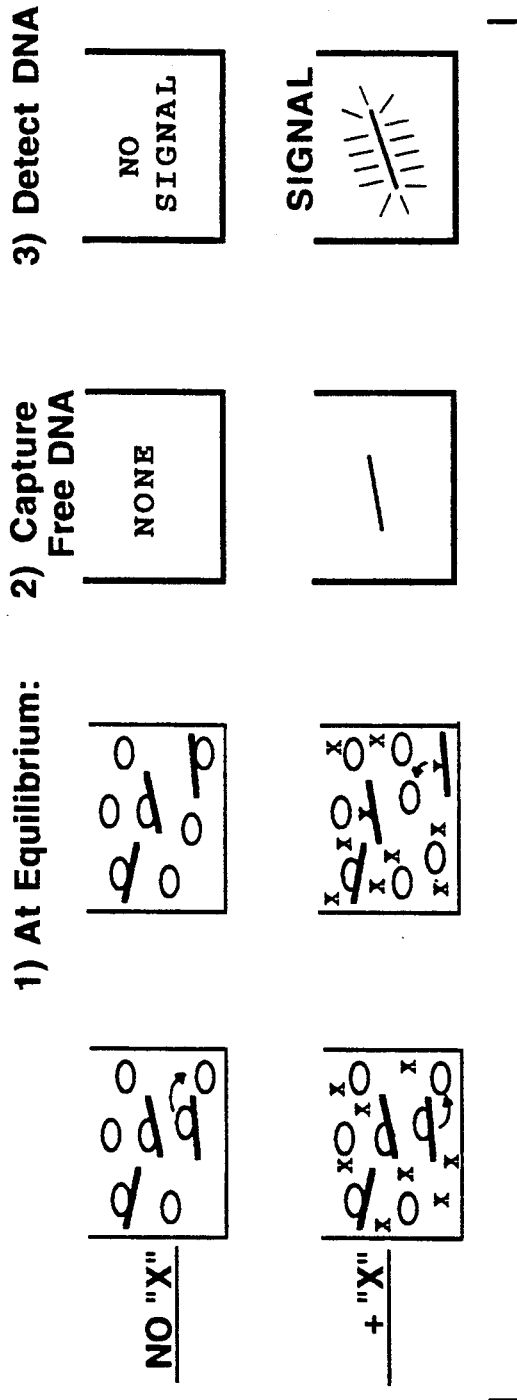
FIG. 2 illustrates an assay for detecting inhibitory molecules based on their ability to preferentially hinder the binding of a DNA-binding protein to its binding site. Protein (O) is displaced from DNA (/) in the presence of inhibitor (X).

As an alternative to the above described band shift gels and filter binding assays, the measurement of inhibitors can be monitored by the level of unbound DNA at equilibrium in the presence of test mixtures. FIG. 2 illustrates an assay for detecting inhibitory molecules based on their ability to preferentially hinder the binding of a DNA-binding protein. In the presence of an inhibitory molecule (X) the equilibrium between the DNA-binding protein and its binding site (screening sequence) is disrupted. The DNA-binding protein (0) is displaced from DNA (/) in the presence of inhibitor (X), the DNA free of protein can then be captured and detected.

For maximum sensitivity, unbound DNA should be sequestered from DNA:protein complexes in an efficient and rapid manner. The method of DNA capture should allow for the rapid removal of the unbound DNA from the protein-rich mixture.

Even if the test molecules are specific in their interaction with DNA they may have relatively low affinity and they may also be weak binders of non-specific DNA or have non-specific interactions with DNA at low concentrations. In either case, their binding to DNA will only be transient, much like the transient binding of the protein in solution. Accordingly, a relevant feature of the assay is to take a molecular snapshot of the equilibrium state of a solution comprised of the target/assay DNA, the protein, and the inhibitory test molecule. In the presence of an inhibitor, the amount of DNA that is not bound to protein will be greater than in the absence of an inhibitor. Any method used to capture the DNA should be rapid, because when the capture system is added to the solution, DNA will be transferred to the capture system at a predetermined rate, based purely on the off-rate of the DNA:protein complex. Unlike the protein and inhibitor, the capture system should bind rapidly and tightly to the DNA. The longer the capture system is left in contact with the solution, the higher the amount of DNA will be captured, regardless of the presence or absence of inhibitor.

One capture system that has been developed in the course of experiments performed in support of the present invention utilizes a streptavidin/biotin interaction. Streptavidin binds with extremely high affinity to biotin ($K_d = 10^{-15}$M) (Chaiet et al.; Green), thus two advantages of the streptavidin/biotin system are that binding between the two molecules is rapid and the interaction is the strongest known non-covalent interaction.

Figure 3:
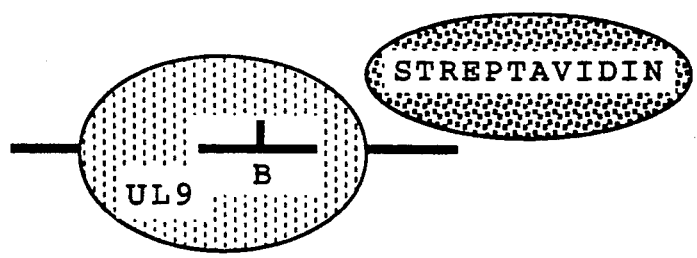
FIG. 3 shows a DNA-binding protein that is able to protect a biotin moiety, covalently attached to the oligonucleotide sequence, from being recognized by the streptavidin when the protein is bound to the DNA.

In this detection system a biotin molecule is covalently attached in the oligonucleotide screening sequence (i.e., the DNA-binding protein's binding site). This attachment is accomplished in such a manner that the binding of the DNA-binding protein to the DNA is not destroyed. Further, when the protein is bound to the biotinylated sequence, the protein prevents the binding of streptavidin to the biotin. In other words, the DNA-binding protein is able to protect the biotin from being recognized by the streptavidin. This DNA:protein interaction is illustrated in FIG. 3.

The capture system is described herein for use with the UL9/oriS system described above. The following general testing principles can, however, be applied to analysis of other DNA:protein interactions. The usefulness of this system depends on the biophysical characteristics of the particular DNA:protein interaction.

Figure 4:
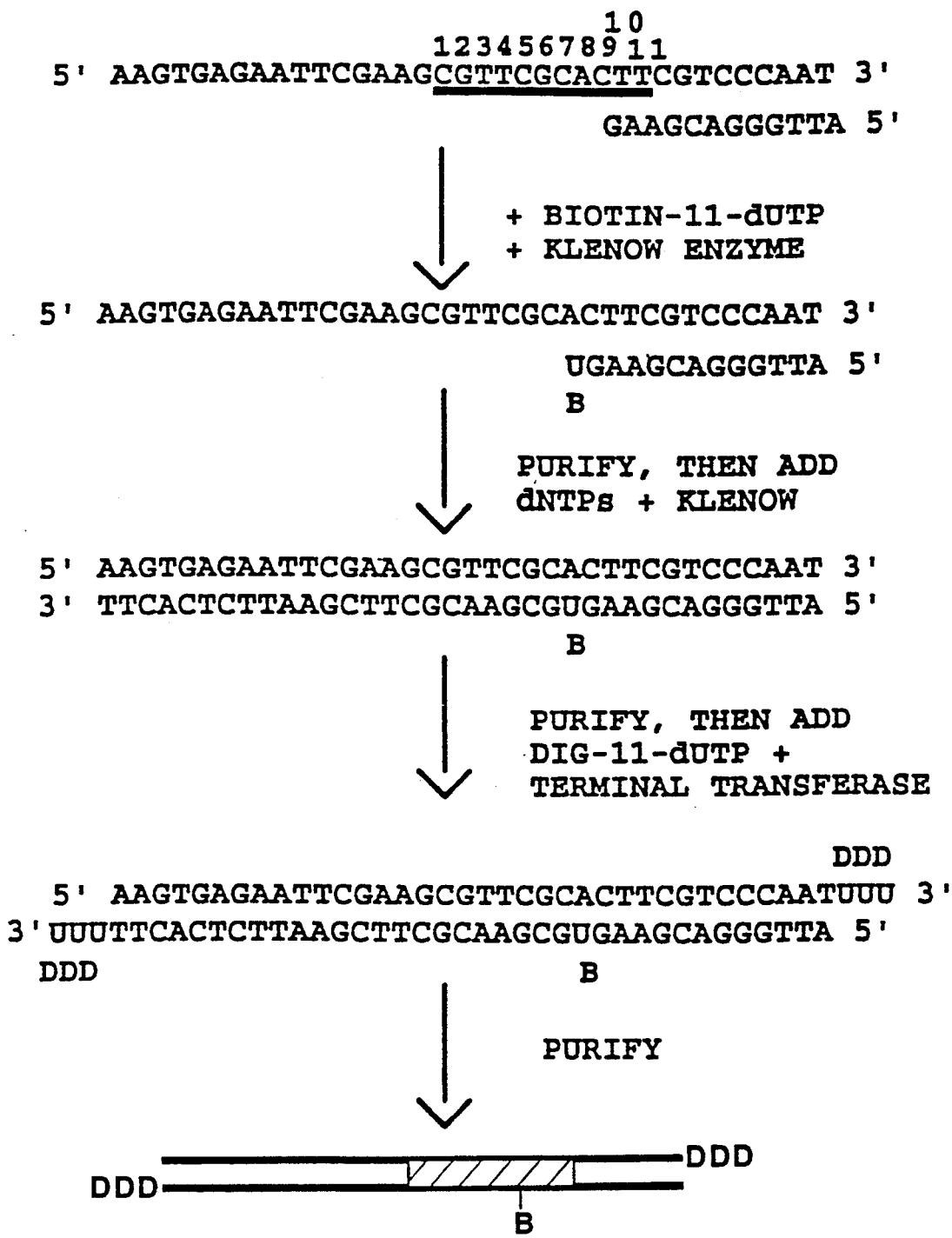
FIG. 4 shows the incorporation of biotin and digoxigenin into a typical oligonucleotide molecule for use in the assay of the present invention. The oligonucleotide contains the binding sequence (i.e., the screening sequence) of the UL9 protein, which is underlined, and test sequences flanking the screening sequence.

The recognition sequence for the binding of the UL9 (Koff et al.) protein is underlined in FIG. 4. Oligonucleotides were synthesized that contain the UL9 binding site and site-specifically biotinylated a number of locations throughout the binding sequence (SEQ ID NO:14; Example 1, FIG. 4). These biotinylated oligonucleotides were then used in band shift assays to determine the ability of the UL9 protein to bind to the oligonucleotide. These experiments using the biotinylated probe and a non-biotinylated probe as a control demonstrate that the presence of a biotin at the #8-T (biotinylated deoxyuridine) position of the bottom strand does not markedly affect the specificity of UL9 for the recognition site: further, streptavidin does not recognize the presence of the biotin moiety. Biotinylation at other A or T positions did not have the two necessary characteristics (i.e., UL9 binding and protection from streptavidin): biotinylation at the adenosine in position #8, of the top strand, prevented the binding of UL9; biotinylation of either adenosines or thymidines (top or bottom strand) at positions #3, #4, #10, or #11 all allowed binding of UL9, but in each case, streptavidin also bound the oligonucleotide in the presence of UL9.

The above result was unexpected in that methylation interference data (Koff et al.) suggest that methylation of the deoxyguanosine residues at positions #7 and #9 of the recognition sequence (on either side of the biotinylated deoxyuridine) blocks UL9 binding. Guanosines are methylated by dimethyl sulfate at the $N^7$ position, which corresponds structurally to the 5-position of the pyrimidine ring at which the deoxyuridine is biotinylated. These moieties all protrude into the major groove of the DNA. The methylation interference data suggest that the #7 and #9 position deoxyguanosines are contact points for UL9, it is therefore unexpected that the presence of a biotin moiety between them does not interfere with binding.

The binding of the full length protein was relatively unaffected by the presence of a biotin at position #8 within the UL9 binding site. The rate of dissociation was similar for full length UL9 with both biotinylated and un-biotinylated oligonucleotides. However, the rate of dissociation of the truncated UL9-COOH polypeptide was faster with the biotinylatd oligonucleotides than with non-biotinylated oligonucleotides, which is a rate comparable to that of the full length protein with either DNA.

The binding conditions were optimized for UL9-COOH so that the off-rate of the truncated UL9 from the biotinylated oligonucleotide was 5–10 minutes (optimized conditions are given in Example 4), a rate compatible with a mass screening assay. The use of multi-well plates to conduct the DNA:protein assay of the present invention is one approach to mass screening.

The streptavidin:biotin interaction can be employed in several different ways to remove unbound DNA from the solution containing the DNA, protein, and test molecule mixture. Magnetic polystyrene or agarose beads, to which streptavidin is covalently attached or attached through a covalently attached biotin, can be exposed to the solution for a brief period, then removed by use, respectively, of magnets or a filter mesh. Magnetic streptavidinated beads are currently the method of choice.

An example of a second method for the removal of unbound DNA is to attach streptavidin to a filter by first linking biotin to the filter, binding streptavidin, then blocking nonspecific sites with a nonspecific protein such as albumin. The mixture is then passed through the filter, unbound DNA is captured and the bound DNA passes through the filter. This method can give high background due to partial retention of the DNA:protein complex on the filter.

One convenient method to sequester captured DNA is the use of streptavidin-conjugated superparamagnetic polystyrene beads as described in Example 7. After capture of DNA, the beads can be retrieved by placing the reaction tubes in a magnetic rack.

Alternatively, avidin-coated agarose beads can be used. Biotinylated agarose beads (immobilized D-biotin, Pierce) are bound to avidin. Avidin, like streptavidin, has four binding sites for biotin. One of these binding sites is used to bind the avidin to the biotin that is coupled to the agarose beads via a 16 atom spacer arm: the other biotin binding sites remain available. The beads are mixed with binding mixtures to capture biotinylated DNA (Example 7). Alternative methods (Harlow et al.) to the bead capture methods just described include the following streptavidinated or avidinated supports: low-protein binding filters, or 96-well plates.

For either of the above bead methods, the beads are isolated and the amount of DNA that has been captured is quantitated. The method of quantitation depends on how the DNA has been prepared. If the DNA is radioactively labelled the beads can be counted in a scintillation counter. Alternatively, the captured DNA may be detecting using a chemiluminescent or colorimetric detection system.

Many of the experiments described above for UL9 DNA:protein-binding studies have made use of radio-labelled oligonucleotides. The techniques involved in radiolabelling of oligonucleotides have been discussed above. A specific activity of $10^8$ dpm per $\mu$g DNA is routinely achieved using standard methods (eg., end-labeling the oligonucleotide with adenosin $\alpha$-[$^{32}$P]-5' triphosphate and T4 polynucleotide kinase). This level of specific activity allows small amounts of DNA to be measured either by autoradiography of gels or filters exposed to film or by direct counting of sample in i0 scintillation fluid.

Radiolabellinq and chemiluminescence (i) are very sensitive, allowing the detection of sub-femtomole quantities of oligonucleotide, and (ii) use well-established techniques. In the case of chemiluminescent detection, protocols have been devised to accommodate the requirements of a mass-screening assay. Non-isotopic DNA detection techniques have principally incorporated alkaline phosphatase as the detectable label given the ability of the enzyme to give a high turnover of substrate to product and the availability of substrates that yield chemiluminescent or colored products.

For chemiluminescent detection, digoxigenin-labelled oligonucleotides (Example 1) can be detected using the chemiluminescent detection system "SOUTHERN LIGHTS," developed by Tropix, Inc. The detection system is diagrammed in FIGS. 11A and 11B. The technique can be applied to detect DNA that has been captured on either beads, filters, or in solution.

Alkaline phosphatase is coupled to the captured DNA without interfering with the capture system. To do this several methods, derived from commonly used ELISA (Harlow et al.; Pierce, Rockford IL) techniques, can be employed. For example, an antigenic moiety is incorporated into the DNA at sites that will not interfere with (i) the DNA:protein interaction, (ii) the DNA:drug interaction, or (iii) the capture system. In the UL9 DNA:protein/biotin system the DNA has been end-labelled with digoxigenin-11-dUTP (dig-dUTP) and terminal transferase (Example 1, FIG. 4). After the DNA was captured and removed from the DNA:protein mixture, an anti-digoxigenin-alkaline phosphatase conjugated antibody was then reacted (Boehringer Mannheim, Indianapolis IN) with the digoxigenin-containing oligonucleotide. The antigenic digoxigenin moiety was recognized by the antibody-enzyme conjugate. The presence of dig-dUTP altered neither the ability of UL9-COOH protein to bind the oriS SEQ ID NO:1-containing DNA nor the ability of streptavidin to bind the incorporated biotin.

Captured DNA was detected using the alkaline phosphatase-conjugated antibodies to digoxygenin as follows. One chemiluminescent substrate for alkaline phosphatase is 3-(2'-spiroadamantane)-4-methoxy-4-(3''-phosphoryloxy) phenyl-1,2-dioxetane disodium salt (AMPPD) (Example 7). Dephosphorylation of AMPPD results in an unstable compound, which decomposes, releasing a prolonged, steady emission of light at 477 nm. Light measurement is very sensitive and can detect minute quantities of DNA (e.g., $10^2$–$10^3$ attomoles) (Example 7).

Colorimetric substrates for the alkaline phosphatase system have also been tested. While the colorimetric substrates are useable, use of the light emission system is more sensitive.

An alternative to the above biotin capture system is to use digoxigenin in place of biotin to modify the oligonucleotide at a site protected by the DNA-binding protein at the assay site: biotin is then used to replace the digoxigenin moieties in the above described detection system. In this arrangement the anti-digoxigenin antibody is used to capture the oligonucleotide probe when it is free of bound protein. Streptavidin conjugated to alkaline phosphatase is then used to detect the presence of captured oligonucleotides.

In addition to identifying molecules or compounds that cause a decreased affinity of the DNA-binding protein for the screening sequence, molecules may be identified that increase the affinity of the protein for its cognate binding site. In this case, leaving the capture system in contact with the assay for increasing amounts of time allows the establishment of a fixed off-rate for the DNA:protein interaction (for example SEQ ID NO:1/UL9). In the presence of a stabilizing molecule, the off-rate, as detected by the capture system time points, will be decreased.

III. Utility

A. Specificity

The present invention defines a high through-put in vitro screening assay to test large libraries of biological or chemical mixtures for the presence of DNA-binding molecules having sequence binding preference. DNA-binding molecules are of particular interest for several reasons:

1) Generally, for a given DNA:protein interaction, there are several thousands fewer target DNA-binding sequences per cell than protein molecules that bind to the DNA. Accordingly, even fairly toxic molecules might be delivered in sufficiently low concentration to exert a biological effect by binding to the target DNA sequences.

2) DNA has a relatively rigid structure compared to RNA or protein. Since the rigid structure reduces possible secondary and tertiary structural variation, finding specific binding molecules should be easier for DNA than for either RNA or protein.

3) Blocking the function of a RNA that encodes a protein or of the protein itself when that protein regulates several cellular genes may have detrimental effects, particularly if some of the regulated genes are important for the survival of the cell. However, blocking a DNA-binding site that is specific to a single gene regulated by such a protein results in reduced toxicity.

An example situation (3) is HNF-1 binding to Hepatitis B virus (HBV): HNF-1 binds an HBV enhancer sequence and stimulates transcription of HBV genes (Chang et al.). In a normal cell HNF-1 is a nuclear protein that appears to be important for the regulation of many liver-specific genes (Courtois et al.). If molecules were isolated that specifically bound to the DNA-binding domain of HNF-1, all of the genes regulated by HNF-1 would be down-regulated. Such a drug could be lethal since many of the genes regulated by HNF-1 may be necessary for cellular liver function. However, the assay of the present invention presents the ability to screen for a molecule that could distinguish the HNF-1 binding region of the Hepatitis B virus DNA from cellular HNF-1 sites by, for example, including divergent flanking sequences when screening for the molecule. Such a molecule would specifically block HBV expression without effecting cellular gene expression.

4) The assay of the present invention is also useful for screening and detecting molecules having preferential DNA sequence binding: Actinomycin D, Distamycin A, and Doxorubicin (Example 6) all provide examples of this type of binding. Many anti-cancer drugs, such as Doxorubicin (see Example 6) show binding preference for some DNA sequences. Doxorubicin is one of the most widely used anti-cancer drugs currently available. As shown in Example 6, Doxorubicin binds some sequences preferentially. Another example of such sequence binding preference is Daunorubicin (Chen et al.) that differs slightly in structure from Doxorubicin (Goodman et al.). Both Daunorubicin and Doxorubicin are members of the anthracycline antibiotic family: antibiotics in this family, and their derivatives, are among the most important newer antitumor agents (Goodman et al.). The assay of the present invention facilitates the identification of other molecules having preferences in DNA sequence binding that can then be subsequently tested for anti-cancer activity through, for example, a battery of assays performed by the National Cancer Institute (Bethesda MD). Further, the assay of the present invention can be used to test derivatives of known anti-cancer agents to examine the effect of the modifications on DNA-binding activity and specificity. The assay provides an initial screen for the design more effective therapeutics.

The screening capacity of this assay is much greater than individually screening binding sequences that have cognate binding proteins. Using the assay of the present invention, libraries of synthetic chemicals or biological molecules can be screened for detecting molecules that have preferential binding to virtually any specified DNA sequence.

B. Sequences Targeted by the Assay

The DNA:protein assay of the present invention has been designed to screen for compounds that bind a full range of DNA sequences that vary in length as well as complexity. Sequence-specific DNA-binding molecules discovered by the assay have potential usefulness as either molecular reagents, therapeutics, or therapeutic precursors. One advantage of the present invention is that the assay is capable of screening for binding activity directed against any DNA sequence. Such sequences can be randomly generated, as could be used for screening for molecules demonstrating sequence preferential binding (like Doxorubicin).

Alternatively, specific test sequences can be chosen which represent medically significant DNA:protein interactions. Examples of such specific sequences are given in Table I.

TABLE I

| MEDICALLY SIGNIFICANT DNA-BINDING SEQUENCES | | |
|---|---|---|
| Test sequence | DNA-binding Protein | Medical Significance |
| EBV origin of replication | EBNA | infectious mononucleosis, nasal pharyngeal carcinoma |
| HSV origin of replication | UL9 | oral and genital Herpes |
| VZV origin of replication | UL9-like | shingles |
| HPV origin of replication | E2 | genital warts, cervical carcinoma |
| Interleukin 2 enhancer | NFAT-1 | immunosuppressant |
| HIV LTR | NFAT-1 NFkB | AIDS, ARC |
| HBV enhancer | HNF-1 | hepatitis |
| Fibrogen promoter | HNF-1 | cardiovascular disease |
| Oncogene promoter and coding sequences | ?? | cancer |

Abbreviations EBV, Epstein-Barr virus; EBNA, Epstein-Barr virus nuclear antigen; HSV, Herpes Simplex virus; VZV, Vericella zoster virus; HPV, human papilloma virus; HIV LTR, Human immunodeficiency virus long terminal repeat; NFAT, nuclear factor of activated T cells; NFkB, nuclear factor kappaB; AIDS, acquired immune deficiency syndrome; ARC, AIDS related complex; HBV, hepatitis B virus; HNF, hepatic nuclear factor.)

The assay has been designed to screen virtually any DNA sequence. Test sequences of medical significance include viral or microbial pathogen genomic sequences and sequences within or regulating the expression of oncogenes or other inappropriately expressed cellular genes.

One consideration in choosing sequences to screen using the assay of the present invention is test sequence accessibility, that is, the potential exposure of the sequence in vivo to binding molecules. Cellular DNA is packaged in chromatin, rendering most sequences relatively inaccessible. Sequences that are actively transcribed, particularly those sequences that are regulatory in nature, are less protected and more accessible to both proteins and small molecules. This observation is substantiated by a large literature on DNAase I sensitivity, footprinting studies with nucleases and small molecules, and general studies on chromatin structure (Tullius). The relative accessibility of a regulatory sequence, as determined by DNAase I hypersensitivity, is likely to be several orders of magnitude greater than an inactive portion of the cellular genome. For this reason the regulatory sequences of cellular genes, as well as viral regulatory or replication sequences, are useful regions to choose for selecting specific inhibitory small molecules using the assay of the present invention.

Another consideration in choosing sequences to be screened using the assay of the present invention is the uniqueness of the potential test sequence. As discussed above for the nuclear protein HNF-1, it is desirable that small inhibitory molecules are specific to their target with minimal cross reactivity. Both sequence composition and length effect sequence uniqueness. Further, certain sequences are found less frequently in the human genome than in the genomes of other organisms, for example, mammalian viruses. Because of base composition and probably codon utilization differences, viral sequences are distinctly different from mammalian sequences. As one example, the dinucleotide CG is found much less frequently in mammalian cells than the dinucleotide sequence GC: further, in SV40, a mammalian virus, the sequences AGCT and ACGT are represented 34 and 0 times, respectively. Specific viral regulatory sequences can be chosen as test sequences keeping this bias in mind. Small inhibitory molecules identified which bind to such test sequences will be less likely to interfere with cellular functions.

In addition to the detection of potential antiviral drugs, the assay of the present invention is also applicable to the detection of potential drugs for disrupting the metabolism of (i) other infectious agents, and (ii) the transcription of inappropriately expressed cellular genes (such as oncogenes or genes associated with certain genetic disorders).

C. Using a Test Matrix

The assay described here has been designed to use a single DNA:protein interaction to screen for sequence-specific and sequence-preferential DNA-binding molecules that can recognize virtually any specified sequence. By using sequences flanking the recognition site for a single DNA:protein interaction, a very large number of different sequences can be tested. The analysis of data yielded by such experiments displayed as matrices should yield more information than data from testing individual sequences that bind a specific protein.

The basic principle behind the DNA:protein assay of the present invention is that when molecules bind DNA sequences flanking the recognition sequence for a specific protein the binding of that protein is blocked. The size of the testable sequences is limited by the distance from the recognition sequence that a small molecule can bind and still interfere with the binding of the protein. Interference with protein binding likely occurs by either (or both) of two mechanisms;

1) directly by steric hindrance, or 2) indirectly by perturbations transmitted to the recognition sequence through the DNA molecule.

Both of these mechanisms will presumably exhibit distance effects. For inhibition by direct steric hindrance direct data for very small molecules is available from methylation and ethylation interference studies. These data suggest that for methyl and ethyl moieties, the steric effect is limited by distance effects to 4-5 base pairs. Even still the number of different sequences that can theoretically be tested for these very small molecules is still very large (i.e., 5 base pair combination total $4^5$ ($-1024$) different sequences).

In practice, the size of sequences tested can be explored empirically for different sized test DNA-binding molecules. A wide array of sequences with increasing sequence complexity can be routinely investigated. This may be accomplished efficiently by synthesizing degenerate oligonucleotides and multiplexing oligonucleotides in the assay process (i.e., using a group of different olignonucleotides in a single assay) or by employing pooled sequences in test matrices.

In view of the above, assays employing a specific protein and oligonucleotides containing the specific recognition site for that protein flanked by different sequences on either side of the recognition site can be used to simultaneously screen for many different molecules, including small molecules, that have binding preferences for individual sequences or families of related sequences. FIG. 12 demonstrates how the analysis of a test matrix yields information about the nature of competitor sequence specificity. As an example, to screen for molecules that could preferentially recognize each of the 256 possible tetranucleotide sequences, oligonucleotides could be constructed that contain these 256 sequences immediately adjacent to a 11 bp recognition sequence of UL9 oriS SEQ ID NO:(15), which is identical in each construct.

In FIG. 12 "+" indicates that the mixture retards or blocks the formation of DNA:protein complexes in solution and "−" indicates that the mixture marked effect on DNA:protein interactions. The results of this test are shown in Table II.

TABLE II

| Oligonucleotide Test Mix | Specificity |
| --- | --- |
| #1,4,7: oligos | none detected for the above |
| #2: for recognition site | either nonspecific or specific |
| #3 | AGCT |
| #5 | CATT or ATT |
| #6 | GCATTC, GCATT, CATTC, GCAT, or ATTC |
| #8 | CTTT |

These results demonstrate how such a matrix provides data on the presence of sequence specific binding activity is a test mixture and also provides inherent controls for non-specific binding.

Typically DNA test sequences, for the assay of the present invention, are double-stranded oligonucleotides (4–50 bp) in length that contain the recognition sequence for a specific DNA-binding protein. The entire DNA molecule containing the screening and test sequences may be larger. Table I lists several potential specific test sequences. As mentioned above, sequence-specific DNA-binding molecules are potentially powerful therapeutics for essentially any disease or condition that in some way involves DNA. Examples of test sequences for the assay include: a) binding sequences of factors involved in the maintenance or propagation of infectious agents, especially viruses, bacteria, yeast and other fungi, b) sequences causing the inappropriate expression of certain cellular genes, and c) sequences involved in the replication of rapidly growing cells. Furthermore, gene expression or replication need not necessarily be disrupted by blocking the binding of specific proteins. Specific sequences within coding regions of genes (e.g., oncogenes) are equally valid test sequences since the binding of small molecules to these sequences is likely to perturb the transcription and/or replication of the region. Finally, any molecules that bind DNA with some sequence specificity, that is, not just to one particular test sequence, may be still be useful as anti-cancer agents. Several small molecules with some sequence preference are already in use as anticancer therapeutics (see Background section). Molecules identified by the present assay may be particularly valuable as lead compounds for the development of congeners (i.e., chemical derivatives of a molecule having difference specificities) with either different specificity or different affinity.

The potential pharmaceutical applications for sequence-specific DNA-binding molecules are very broad, including antiviral, antifungal, antibacterial, antitumor agents, immunosuppressants, and cardiovascular drugs.

Sequence-specific DNA-binding molecules can also be useful as molecular reagents as, for example, specific sequence probes.

As more molecules are detected, information about the nature of DNA-binding molecules will be gathered, eventually facilitating the design and/or modification of new molecules with different or specialized activities.

Although the assay has been described in terms of the detection of sequence-specific DNA-binding molecules, the reverse assay could be achieved by adding DNA in excess to protein to look for peptide sequence specific protein-binding inhibitors.

The following examples illustrate, but in no way are intended to limit the present invention.

MATERIALS AND METHODS

Synthetic oligonucleotides were prepared using commercially available automated oligonucleotide synthesizers. Alternatively, custom designed synthetic oligonucleotides may be purchased, for example, from Synthetic Genetics (San Diego, Calif.). Complementary strands were annealed to generate double-strand oligonucleotides.

Restriction enzymes were obtained from Boehringer Mannheim (Indianapolis Ind.) or New England Biolabs (Beverly Ma.) and were used as per the manufacturer's directions.

Distamycin A and Doxorubicin were obtained from Sigma (St. Louis, Mo.). Actinomycin D was obtained from Boehringer Mannheim or Sigma.

EXAMPLE 1

Preparation of the Oligonucleotide Containing the Screening sequence

This example describes the preparation of (i) biotinylated/digoxyginin/radiolabelled, and (ii) radiolabelled double-stranded oligonucleotides that contain the screening sequence and selected Test sequence.

A. Biotinylation

The oligonucleotides were prepared as described above. The wild-type control sequence for the UL9 binding site, as obtained from HSV, is shown in FIG. 4. The screening sequence, i.e. The UL9 binding sequence, is CGTTCGCACTT (SEQ ID NO:1) and is underlined in FIG. 4. Typically, sequences 5' and/or 3' to the screening sequence were replaced by a selected Test sequence (FIG. 5).

One example of the preparation of a site-specifically biotinylated oligonucleotide is outlined in FIG. 4. An oligonucleotide primer complementary to the 3' sequences of the screening sequence-containing oligonucleotide was synthesized. This oligonucleotide terminated at the residue corresponding to the C in position 9 of the screening sequence. The primer oligonucleotide was hybridized to the oligonucleotide containing the screening sequence. Biotin-11-dUTP (Bethesda Research Laboratories (BRL), Gaithersburg Md.) and Klenow enzyme were added to this complex (FIG. 4) and the resulting partially double-stranded biotinylated complexes were separated from the unincorporated nucleotides using either pre-prepared G-25 Sephadex spin columns (Pharmacia, Piscataway N.J.) or "NENSORB" columns (New England Nuclear) as per manufacturer's instructions. The remaining single-strand region was converted to double-strands using DNA polymerase I Klenow fragment and dNTPs resulting in a fully double-stranded oligonucleotide. A second G-25 Sephadex column was used to purify the double-stranded oligonucleotide. Oligonucleotides were diluted or resuspended in 10 mM Tris-HCl, pH 7.5, 50 mM NaCl, and 1 mM EDTA and stored at −20° C. For radiolabelling the complexes, $^{32}$P-alpha-dCTP (New England Nuclear, Wilmington, Del.) replaced dCTP for the double-strand completion step. Alternatively, the top strand, the primer, or the fully double-stranded oligonucleotide was radiolabeled with $\gamma$-$^{32}$P-ATP and polynucleotide kinase (NEB, Beverly, Ma.). The reaction conditions for all of the above Klenow reactions were as follows: 10 mM Tris-HCl, pH 7.5, 10 mM MgCl$_2$, 50 mM NaCl, 1 mM dithioerythritol, 0.33–100 $\mu$M deoxytriphosphates, 2 units Klenow enzyme (Boehringer-Mannheim, Indianapolis Ind.). The Klenow reactions were incubated at 25° C. for 15 minutes to 1 hour. The polynucleotide kinase reactions were incubated at 37° C. for 30 minutes to 1 hour.

The biotinylated, radiolabelled oligonucleotides were isolated as above and resuspended in 0.2 M potassium cacodylate (pH=7.2), 4 mM MgCl$_2$, 1 mM 2-mercaptoethanol, and 0.5 mg/ml bovine serum albumin. To this reaction mixture digoxigenin-11-dUTP (an analog of dTTP, 2'-deoxyuridine-5'-triphosphate, coupled to digoxigenin via an 11-atom spacer arm, Boehringer Mannheim, Indianapolis Ind.) and terminal deoxynucleotidyl transferase (GIBCO BRL, Gaithersburg, Md.) were added. The number of Dig-11-dUTP moieties incorporated using this method appeared to be less than 5 (probably only 1 or 2) as judged by electrophoretic mobility on polyacrylamide gels of the treated fragment as compared to oligonucleotides of known length.

The biotinylated, digoxygenin-containing, radiolabelled oligonucleotides were isolated as above and resuspended in 10 mM Tris-HCl, 1 mM EDTA, 50 mM NaCl, pH 7.5 for se in the binding assays.

The above procedure can also be used to biotinylate the other strand by using an oligonuoleotide containing the screening sequence complementary to the one shown in FIG. 4 and a primer complementary to the 3' end of that molecule. To accomplish the biotinylation Biotin-7-dATP was substituted for Biotin-11-dUTP. Biotinylation was also accomplished by chemical synthetic methods: for example, an activated nucleotide is incorporated into the oligonucleotide and the active group is subsequently reacted with NHS-LC-Biotin (Pierce). Other biotin derivatives can also be used.

B. Radiolabelling the Oligonucleotides

Generally, oligonucleotides were radiolabelled with gamma-$^{32}$P-ATP or alpha-$^{32}$P-deoxynucleotide triphosphates and T4 polynucleotide kinase or the Klenow fragment of DNA polymerase, respectively. Labelling reactions were performed in the buffers and by the methods recommended by the manufacturers (New England Biolabs, Beverly Ma.; Bethesda Research Laboratories, Gaithersburg Md.; or Boehringer/Mannheim, Indianapolis Ind.). Oligonucleotides were separated from buffer and unincorporated triphosphates using G-25 Sephadex preformed spin columns (IBI, New Haven, Conn.; or Biorad, Richmond, Calif.) or "NENSORB" preformed columns (New England Nuclear, Wilmington, Del.) as per the manufacturers instructions.

EXAMPLE 2

Preparation of the UL9 Protein

A. Cloning of the UL9 Coding Sequences into pAC373

To express full length UL9 protein a baculovirus expression system has been used. The sequence of the UL9 coding region of Herpes Simplex Virus has been disclosed by McGeoch et al. and is available as an EMBL nucleic acid sequence. The recombinant baculovirus AcNPV/UL9A, which contained the UL9 coding sequence, was obtained from Mark Challberg (National Institutes of Health, Bethesda Md.). The construction of this vector has been previously described (Olivo et al. (1988, 1989)). Briefly, the NarI/EcoRV fragment was derived from pMC160 (Wu et al.). Blunt-ends were generated on this fragment by using all four dNTPs and the Klenow fragment of DNA polymerase I (Boehringer Mannheim, Indianapolis IN) to fill in the terminal overhangs. The resulting fragment was blunt-end ligated into the unique BamHI site of the baculoviral vector pAC3T3 (Summers et al.).

B. Cloning of the UL9 Coding Sequence in pVL-1393

The UL9 coding region was cloned into a second baculovirus vector, pVL1393 (Luckow et al.). The 3077 bp NarI/EcoRV fragment containing the UL9 gene was excised from vector pEcoD (obtained from Dr. Bing Lan Rong, Eye Research Institute, Boston, Ma.): the plasmid pEcoD contains a 16.2 kb EcoRI fragment derived from HSV-I that bears the UL9 gene (Goldin et al.). Blunt-ends were generated on the UL9-containing fragment as described above. EcoRI linkers (10 mer) were blunt-end ligated (Ausubel et al.; Sambrook et al.) to the blunt-ended NarI/EcoRV fragment.

Figure 7:
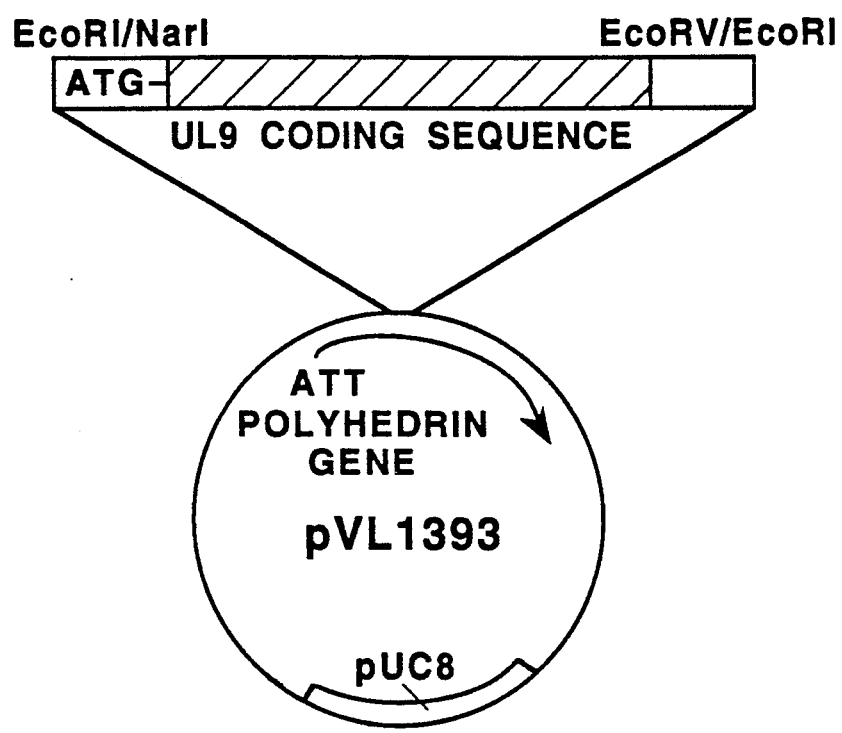
FIG. 7 shows the pVL1393 baculovirus vector containing the full length UL9 protein coding sequence.

The vector pVL1393 (Luckow et al.) was digested with EcoRI and the linearized vector isolated. This vector contains 35 nucleotides of the 5' end of the coding region of the polyhedron gene upstream of the polylinker cloning site. The polyhedron gene ATG has been mutated to ATT to prevent translational initiation in recombinant clones that do not contain a coding sequence with a functional ATG. The EcoRI/UL9 fragment was ligated into the linearized vector, the ligation mixture transformed into E. coli and ampicillin resistant clones selected. Plasmids recovered from the clones were analyzed by restriction digestion and plasmids carrying the insert with the amino terminal UL9 coding sequences oriented to the 5' end of the polyhedron gene were selected. This plasmid was designated pVL1393/UL9 (FIG. 7).

pVL1393/UL9 was cotransfected with wild-type baculoviral DNA (AcMNPV; Summers et al.) into SF9 (*Spodoptera frugiperda*) cells (Summers et al.) Recombinant baculovirus-infected Sf9 cells were identified and clonally purified (Summers et al.).

C. Expression of the UL9 Protein

Clonal isolates of recombinant baculovirus infected Sf9 cells were grown in Grace's medium as described by Summers et al. The cells were scraped from tissue culture plates and collected by centrifugation (2,000 rpm, for 5 minutes, 4° C.). The cells were then washed once with phosphate buffered saline (PBS) (Maniatis et al.). Cell pellets were frozen at −70° C. For lysis the cells were resuspended in 1.5 volumes 20 mM HEPES, pH 7.5, 10% glycerol, 1.7 M NaCl, 0.5 mM EDTA, 1 mM dithiothreitol (DTT), and 0.5 mM phenyl methyl sulfonyl fluoride (PMSF). Cell lysates were cleared by ultracentrifugation (Beckman table top ultracentrifuge, TLS 55 rotor, 34 krpm, 1 hr, 4° C.). The supernatant was dialyzed overnight at 4° C. against 2 liters dialysis buffer (20 mM HEPES, pH 7.5, 10% glycerol, 50 mM NaCl, 0.5 mM EDTA, 1 mM dtt, and 0.1 mM PMSF).

These partially purified extracts were prepared and used in DNA:protein binding experiments. If necessary extracts were concentrated using a "CENTRICON 30" filtration device (Amicon, Danvers Ma.).

D. Cloning the Truncated UL9 Protein

Figure 6:
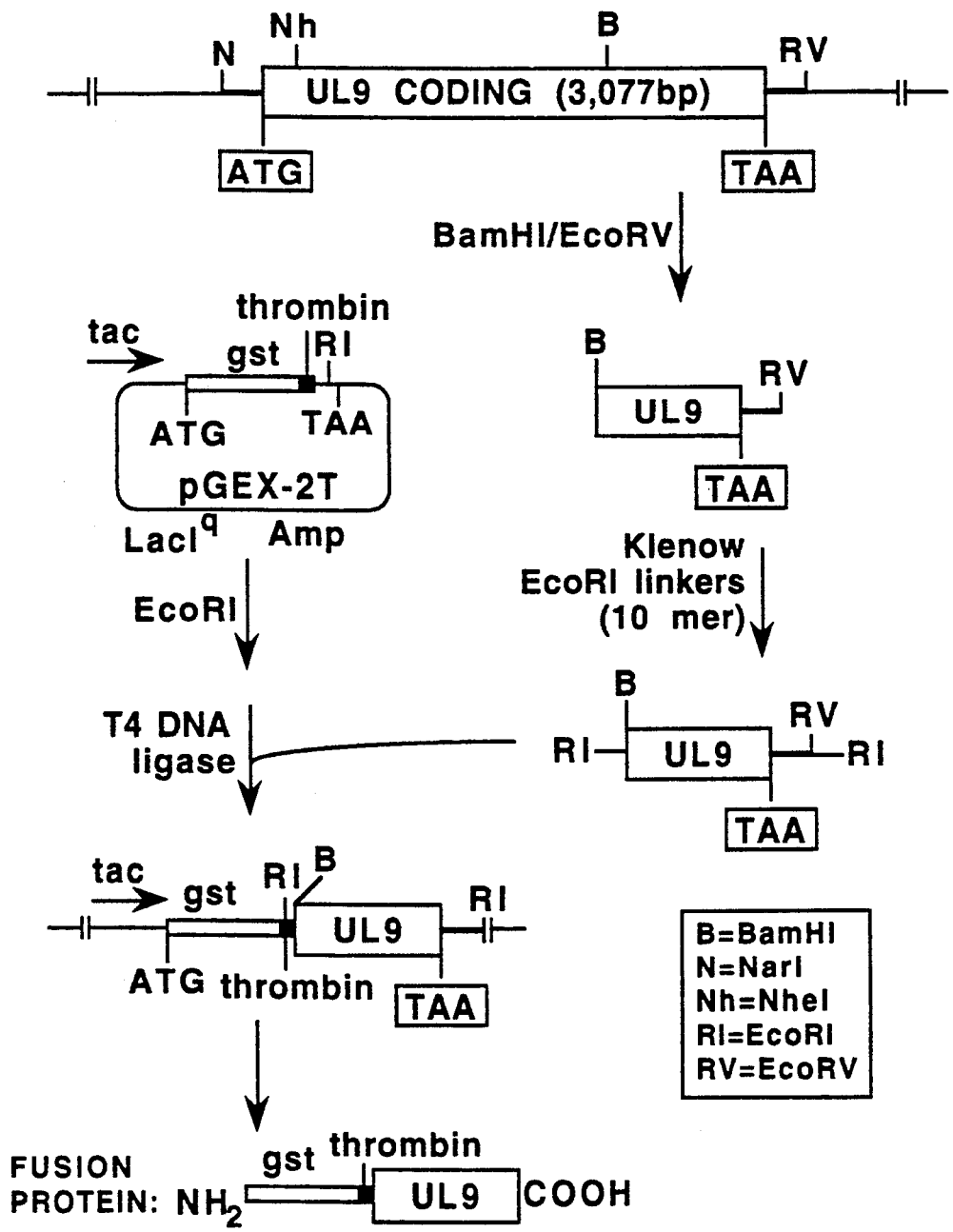
FIG. 6 outlines the cloning of a truncated form of the UL9 protein, which retains its sequence-specific DNA-binding ability (UL9-COOH), into an expression vector.

The sequence encoding the C-terminal third of UL9 and the 3' flanking sequences, an approximately 1.2 kb fragment, was subcloned into the bacterial expression vector, pGEX-2T (FIG. 6). The pGEX-2T is a modification of the pGEX-1 vector of Smith et al. which involved the insertion of a thrombin cleavage sequence in-frame with the glutathione-S-transferase protein (gst).

A 1,194 bp BamHI/EcoRV fragment of pEcoD was isolated that contained a 951 bp region encoding the C-terminal 317 amino acids of UL9 and 243 bp of the 3' untranslated region.

This BamHI/EcoRV UL9 carboxy-terminal (UL9-COOH) containing fragment was blunt-ended and EcoRI linkers added as described above. The EcoRI linkers were designed to allow in-frame fusion of the UL9 coding sequence to the gst-thrombin coding sequences. The linkered fragment was isolated and digested with EcoRI. The pGEX-2T vector was digested with EcoRI, treated with Calf Intestinal Alkaline Phosphatase (CIP) and the linear vector isolated. The EcoRI linkered UL9-COOH fragment was ligated to the linear vector (FIG. 6). The ligation mixture was transformed into *E. coli* and ampicillin resistant colonies were selected. Plasmids were isolated from the ampicillin resistant colonies and analyzed by restriction enzyme digestion. A plasmid which generated a gst/thrombin/UL9-COOH in frame fusion was identified (FIG. 6) and designated pGEX-2T/UL9-COOH.

D. Expression of the Truncated UL9 Protein.

*E. coli* strain JM109 was transformed with pGEX-2T/C-UL9-COOH and was grown at 37° C. to saturation density overnight. The overnight culture was diluted 1:10 with LB medium containing ampicillin and grown from one hour at 30° C. IPTG (isopropyllthio-$\beta$-galactoside) (GIBCO-BRL) was added to a final concentration of 0.1 mM and the incubation was continued for 2-5 hours. Bacterial cells containing the plasmid were subjected to the temperature shift and IPTG conditions, which induced transcription from the tac promoter.

Cells were harvested by centrifugation and resuspended in 1/100 culture volume of MTPBS (150 mM NaCl, 16 mM Na$_2$HPO$_4$, 4 mM NaH$_2$PO$_4$). Cells were lysed by sonication and lysates cleared of cellular debris by centrifugation.

The fusion protein was purified over a glutathione agarose affinity column as described in detail by Smith et al. The fusion protein was eluted from the affinity column with reduced glutathione, dialyzed against UL9 dialysis buffer (20 mM HEPES pH 7.5, 50 mM NaCl, 0.5 mM EDTA, 1 mM DTT, 0.1 mM PMSF) and cleaved with thrombin (2 ng/ug of fusion protein).

An aliquot of the supernatant obtained from IPTG-induced cultures of pGEX-2T/C-UL9-COOH-containing cells and an aliquot of the affinity-purified, thrombin-cleaved protein were analyzed by SDS-polyacrylamide gel electrophoresis. The result of this analysis is shown in FIG. 8. The 63 kilodalton GST/C-UL9 fusion protein is the largest band in the lane marked GST-UL9 (lane 2). The first lane contains protein size standards. The UL9-COOH protein band (lane GST-UL9+Thrombin, FIG. 8, lane 3) is the band located between 30 and 46 kD: the glutathione transferase protein is located just below the 30 kD size standard. In a separate experiment a similar analysis was performed using the uninduced culture: it showed no protein corresponding in size to the fusion protein.

Extracts are dialyzed before use. Also, if necessary, the extracts can be concentrated typically by filtration using a "CENTRICON 30" filter.

EXAMPLE 3

Binding Assays

A. Band shift gels

DNA:protein binding reactions containing both labelled complexes and free DNA were separated electrophoretically on 4-10% polyacrylamide/Tris-Borate-EDTA (TBE) gels (Freid et al.; Garner et al.). The gels were then fixed, dried, and exposed to X-ray film. The autoradiograms of the gels were examined for band shift patterns.

B. Filter Binding Assays

A second method used particularly in determining the off-rates for protein:oligonucleotide complexes is filter binding (Woodbury et al.). Nitrocellulose disks (Schleicher and Schuell, BA85 filters) that have been soaked in binding buffer (see below) were placed on a vacuum filter apparatus. DNA:protein binding reactions (see below; typically 15-30 $\mu$l) are diluted to 0.5 ml with binding buffer (this dilutes the concentration of components without dissociating complexes) and applied to the discs with vacuum applied. Under low salt conditions the DNA:protein complex sticks to the filter while free DNA passes through. The discs are placed in scintillation counting fluid (New England Nuclear), and the cpm determined using a scintillation counter.

This technique can be adapted to 96-well nitrocellulose filtration plates (Millipore) using the above protocol except (i) the reaction dilution and wash volumes are reduced and (ii) the flow rate through the filter can be controlled by adjusting the vacuum pressure.

EXAMPLE 4

Functional UL9 Binding Assay

A. Functional DNA-binding Activity Assay

Purified protein was tested for functional activity using band-shift assays. Radiolabelled oligonucleotides (prepared as in Example 1B) that contain the 11 bp recognition sequence were mixed with the UL9 protein in binding buffer (optimized reaction conditions: 0.1 ng $^{32}$P-DNA, 1 ul UL9 extract, 20 mM HEPES, pH 7.2, 50 mM KCl, and 1 mM DTT). The reactions were incubated at room temperature for 10 minutes (binding occurs in less than 2 minutes), then separated electrophoretically on 4-10% non-denaturing polyacrylamide gels. UL9-specific binding to the oligonucleotide is indicated by a shift in mobility of the oligonucleotide on the gel in the presence of the UL9 protein but not in its absence. Bacterial extracts containing (+) or without (−) UL9 protein and affinity purified UL9 protein were tested in the assay. Only bacterial extracts containing UL9 or affinity purified UL9 protein generate the gel band-shift indicating protein binding.

The degree of extract that needed to be added to the reaction mix, in order to obtain UL9 protein excess relative to the oligonucleotide, was empirically determined for each protein preparation/extract. Aliquots of the preparation were added to the reaction mix and treated as above. The quantity of extract at which the majority of the labelled oligonucleotide appears in the DNA:protein complex was evaluated by band-shift or filter binding assays. The assay is most sensitive under conditions in which the minimum amount of protein is added to bind most of the DNA. Excess protein can decrease the sensitivity of the assay.

B. Rate of Dissociation

The rate of dissociation is determined using a competition assay. An oligonucleotide having the sequence presented in FIG. 4, which contained the binding site for UL9 (SEQ ID NO:14), was radiolabelled with $^{32}$P-ATP and polynucleotide kinase (Bethesda Research Laboratories). The competitor DNA was a 17 base pair oligonucleotide (SEQ ID NO:16) containing the binding site for UL9.

In the competition assays, the binding reactions (Example 4A) were assembled with each of the oligonucleotides and placed on ice. Unlabelled oligonucleotide (1 $\mu$g) was added 1, 2, 4, 6, or 21 hours before loading the reaction on an 8% polyacrylamide gel (run in TBE buffer (Maniatis et al.)) to separate the reaction components. The dissociation rates, under these conditions, for the truncated UL9 (UL9-COOH) and the full length UL9 is approximately 4 hours at 4° C. In addition, random oligonucleotides (a 10,000-fold excess) that did not contain the UL9 binding sequence and sheared herring sperm DNA (a 100,000-fold excess) were tested: neither of these control DNAs competed for binding with the oligonucleotide containing the UL9 binding site.

C. Optimization of the UL9 Binding Assay (i) Truncated UL9 from the bacterial expression system The effects of the following components on the binding and dissociation rates of UL9-COOH with its cognate binding site have been tested and optimized: buffering conditions (including the pH, type of buffer, and concentration of buffer); the type and concentration of monovalent cation; the presence of divalent cations and heavy metals; temperature; various polyvalent cations at different concentrations; and different redox reagents at different concentrations. The effect of a given component was evaluated starting with the reaction conditions given above and based on the dissociation reactions described in Example 4B.

The optimized conditions used for the binding of UL9-COOH contained in bacterial extracts (Example 2E) to oligonucleotides containing the HSV ori sequence (SEQ ID NO:1) were as follows: 20 mM HEPES, pH 7.2, 50 mM KCl, 1 mM DTT, 0.005–0.1 ng radiolabeled (specific activity, approximately $10^8$ cpm/$\mu$g) or digoxiginated, biotinylated oligonucleotide probe, and 5–10 $\mu$g crude UL9-COOH protein preparation (1 mM EDTA is optional in the reaction mix). Under optimized conditions, UL9-COOH binds very rapidly and has a dissociation rate of about 4 hours at 4° C. with non-biotinylated oligonucleotide and 5–10 minutes with biotinylated oligonucleotides. The dissociation rate of UL9-COOH changes markedly under different physical conditions. Typically, the activity of a UL9 protein preparation was assessed using the gel band-shift assay and related to the total protein content of the extract as a method of standardization. The addition of herring sperm DNA depended on the purity of UL9 used in the experiment Binding assays were incubated at 25° C. for 5–30 minutes.

(ii) Full length UL9 protein from the baculovirus system

The binding reaction conditions for the full length baculovirus-produced UL9 polypeptide have also been optimized. The optimal conditions for the current assay were determined to be as follows: 20 mM Hepes; 100 mM NaCl; 0.5 mM dithiothreitol; 1 mM EDTA; 5% glycerol; from 0 to $10^4$-fold excess of sheared herring sperm DNA; 0.005–0.1 ng radiolabeled (specific activity, approximately 10: cpm/$\mu$g) or digoxiginated, biotinylated oligonucleotide probe, and 5–10 $\mu$g crude UL9 protein preparation. The full length protein also binds well under the optimized conditions established for the truncated UL9-COOH protein.

EXAMPLE 5

The Effect of Test Sequence Variation on the Off-Rate of the UL9 Protein

Figure 9:
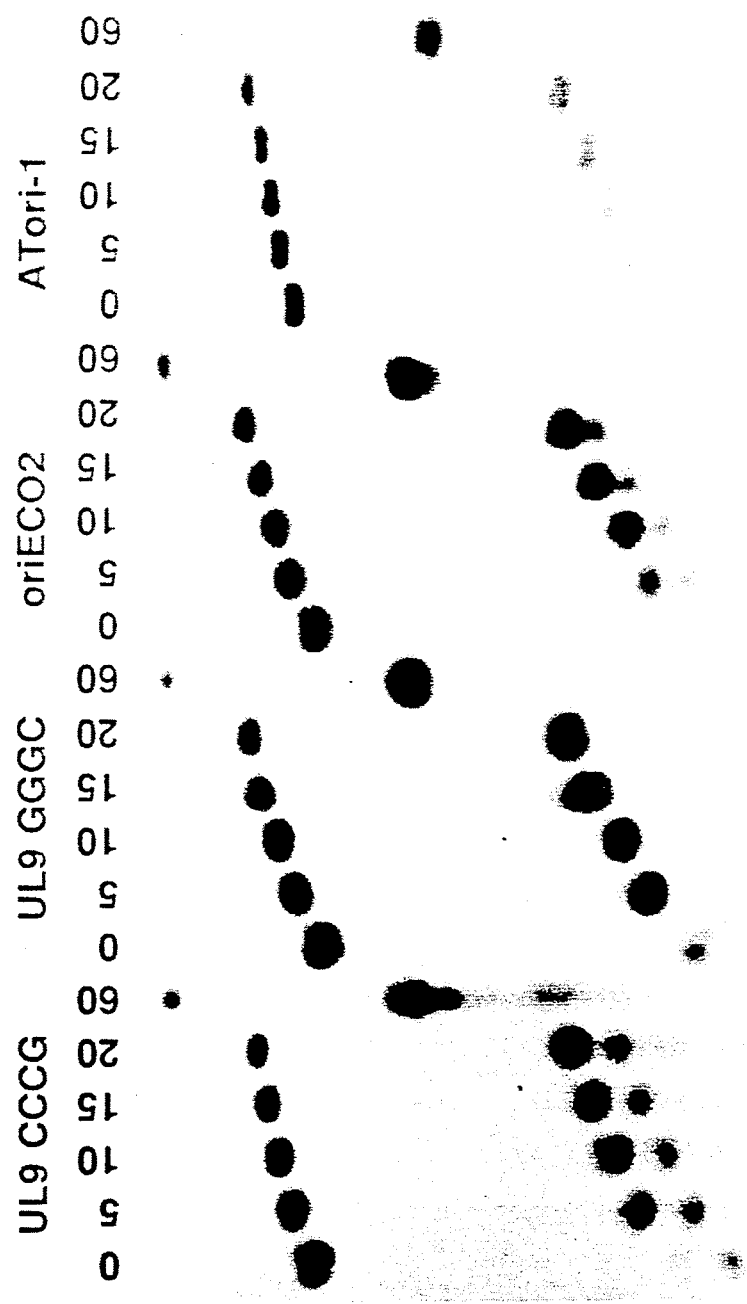
FIG. 9 shows the effect on UL9-COOH binding of alterations in the test sequences that flank the UL9 screening sequence.

The oligonucleotides shown in FIG. 5 were radiolabelled as described above. The competition assays were performed as described in Example 4B using UL9-COOH. Radiolabelled oligonucleotides were mixed with the UL9-COOH protein in binding buffer (typical reaction: 0.1 ng oligonucleotide $^{32}$P-DNA, 1 $\mu$l UL9-COOH extract, 20 mM HEPES, pH 7.2, 50 mM KCl, 1 mM EDTA, and 1 mM DTT). The reactions were incubated at room temperature for 10 minutes. A zero time point sample was then taken and loaded onto an 8% polyacrylamide gel (run use TBE). One $\mu$g of the unlabelled 17 bp competitive DNA oligonucleotide (SEQ ID NO;16) (Example 4B) was added at 5, 10, 15, 20, or 60 minutes before loading the reaction sample on the gel. The results of this analysis are shown in FIG. 9: the screening sequences that flank the UL9 binding site (SEQ ID NO:5-SEQ ID NO:13) are very dissimilar but have little effect on the off-rate of UL9. Accordingly, these results show that the UL9 DNA binding protein is effective to bind to a screening sequence in duplex DNA with a binding affinity that is substantially independent of est sequences placed adjacent the screening sequence. Filter binding experiments gave the same result.

EXAMPLE 6

The Effect of Actinomycin D, Distamycin A, and Doxorubicin on UL9 Binding to the screening Sequence is Dependent on the Specific Test Sequence Different oligonucleotides, each of which contained the screening sequence (SEQ ID NO:1) flanked on the 5' and 3' sides by a test sequence (SEQ ID NO:5 to SEQ ID NO:13), were evaluated for the effects of distamycin A, actinomycin D, and doxorubicin on UL9-COOH binding.

Binding assays were performed as described in Example 5. The oligonucleotides used in the assays are shown in FIG. 5. The assay mixture was allowed to pre-equilibrate for 15 minutes at room temperature prior to the addition of drug.

A concentrated solution of Distamycin A was prepared in dH$_2$O and was added to the binding reactions at the following concentrations: 0, 1 $\mu$M, 4 $\mu$M, 16 $\mu$M, and 40 $\mu$M. The drug was added and incubated at room temperature for 1 hour. The reaction mixtures were then loaded on an 8% polyacrylamide gel (Example 5) and the components separated electrophoretically. Autoradiographs of these gels are shown in FIG. 10A. The test sequences tested were as follows: UL9 polyT, SEQ ID NO:9; UL9 CCCG, SEQ ID NO:5; UL9 GGGC, SEQ ID NO:6; UL9 polyA, SEQ ID NO:8; and UL9 ATAT, SEQ ID NO:7. These results demonstrate that Distamycin A preferentially disrupts binding to UL9 polyT, UL9 polyA and UL9 ATAT.

A concentrated solution of Actinomycin D was prepared in dH$_2$O and was added to the binding reactions at the following concentrations: 0 $\mu$M and 50 $\mu$M. The drug was added and incubated at room temperature for 1 hour.

Equal volumes of dH$_2$O were added to the control samples. The reaction mixtures were then loaded on an 8% polyacrylamide gel (Example 5) and the components separated electrophoretically. Autoradiographs of these gels are shown in FIG. 10B. In addition to the test sequences tested above with Distamycin A, the following test sequences were also tested with Actinomycin D: ATori1, SEQ ID NO:11; oriEco2, SEQ ID NO:12, and oriEco3, SEQ ID NO:13. These results demonstrate that actinomycin D preferentially disrupts the binding of UL9 to the oligonucleotides UL9 CCCG and UL9 GGGC.

A concentrated solution of Doxorubicin was prepared in dH$_2$O and was added to the binding reactions at the following concentrations: 0 μM, 15 μM and 35 μM. The drug was added and incubated at room temperature for 1 hour. Equal volumes of dH$_2$O were added to the control samples. The reaction mixtures were then loaded on an 8% polyacrylamide gel (Example 5) and the components separated electrophoretically. Autoradiographs of these gels are shown in FIG. 10C. The same test sequences were tested as for Actinomycin D. These results demonstrate that Doxorubicin preferentially disrupts the binding of UL9 to the oligonucleotides UL9polyT, UL9 GGGC, oriEco2, and oriEco3. Doxorubicin appears to particularly disrupt the UL9:screening sequence interaction when the test sequence oriEco3 is used. The sequences of the test sequences for oriEco2 and oriEco3 differ by only one base: an additional T residue inserted at position 12, compare SEQ ID NO:12 and SEQ ID NO:13.

EXAMPLE 7

Use of the Biotin/Streptavidin Reporter System

A. The Capture of Protein-Free DNA

Several methods have been employed to sequester unbound DNA from DNA:protein complexes.

(i) Magnetic beads

Streptavidin-conjugated superparamagnetic polystyrene beads (Dynabeads M-280 Streptavidin, Dynal AS, 6–7×10$^8$ beads/ml) are washed in binding buffer then used to capture biotinylated oligonucleotides (Example 1). The beads are added to a 15 ul binding reaction mixture containing binding buffer and biotinylated oligonucleotide. The beads/oligonucleotide mixture is incubated for varying lengths of time with the binding mixture to determine the incubation period to maximize capture of protein-free biotinylated oligonucleotides. After capture of the biotinylated oligonucleotide, the beads can be retrieved by placing the reaction tubes in a magnetic rack (96-well plate magnets are available from Dynal). The beads are then washed.

(ii) Agarose beads

Biotinylated agarose beads (immobilized D-biotin, Pierce, Rockford, IL) are bound to avidin by treating the beads with 50 μg/μl avidin in binding buffer overnight at 4° C. The beads are washed in binding buffer and used to capture biotinylated DNA. The beads are mixed with binding mixtures to capture biotinylated DNA. The beads are removed by centrifugation or by collection on a non-binding filter disc.

For either of the above methods, quantification of the presence of the oligonucleotide depends on the method of labelling the oligonucleotide. If the oligonucleotide is radioactively labelled: (i) the beads and supernatant can be loaded onto polyacrylamide gels to separate protein:DNA complexes from the bead:DNA complexes by electrophoresis, and autoradiography performed; (ii) the beads can be placed in scintillation fluid and counted in a scintillation counter. Alternatively, presence of the oligonucleotide can be determined using a chemiluminescent or colorimetric detection system.

B. Detection of Protein-Free DNA

The DNA is end-labelled with digoxigenin-11-dUTP (Example 1). The antigenic digoxigenin moiety is recognized by an antibody-enzyme conjugate, anti-digoxigenin-alkaline phosphatase (Boehringer Mannheim Indianapolis Ind.). The DNA/antibody-enzyme conjugate is then exposed to the substrate of choice. The presence of dig-dUTP does not alter the ability of protein to bind the DNA or the ability of streptavidin to bind biotin.

(i) Chemiluminescent Detection

Digoxigenin-labelled oligonucleotides are detected using the chemiluminescent detection system "SOUTHERN LIGHTS" developed by Tropix, Inc. (Bedford, Ma.). Use of this detection system is illustrated in FIG. 11A and 11B. The technique can be applied to detect DNA that has been captured on either beads or filters.

Biotinylated oligonucleotides, which have terminal digoxygenin-containing residues (Example 1), are captured on magnetic (FIG. 11A) or agarose beads (FIG. 11B) as described above. The beads are isolated and treated to block non-specific binding by incubation with I-Light blocking buffer (Tropix) for 30 minutes at room temperature. The presence of oligonucleotides is detected using alkaline phosphatase-conjugated antibodies to digoxygenin. Anti-digoxigenin-alkaline phosphatase (anti-dig-AP, 1:5000 dilution of 0.75 units/ul, Boehringer Mannheim) is incubated with the sample for 30 minutes, decanted, and the sample washed with 100 mM Tris-HCl, pH 7.5, 150 mM NaCl. The sample is pre-equilibrated with 2 washes of 50 mM sodium bicarbonate, pH 9.5, 1 M MgCl$_2$, then incubated in the same buffer containing 0.25 mM 3-(2'-spiroadamantane)-4-methoxy-4-(3'-phosphoryloxy) phenyl-1,2-dioxetane disodium salt (AMPPD) for 5 minutes at room temperature. AMPPD was developed (Tropix Inc.) as a chemiluminescent substrate for alkaline phosphatase. Upon dephosphorylation of AMPPD the resulting compound decomposes, releasing a prolonged, steady emission of light at 477 nm.

Excess liquid is removed from filters and the emission of light occurring as a result of the dephosphorylation of AMPPD by alkaline phosphatase can be measured by exposure to x-ray film or by detection in a luminometer.

In solution, the bead-DNA-anti-dig-AP is resuspended in "SOUTHERN LIGHT" assay buffer and AMPPD and measured directly in a luminometer. Large scale screening assays are performed using a 96-well plate-reading luminometer (Dynatech Laboratories, Chantilly, Va.). Subpicogram quantities of DNA ($10^2$ to $10^3$ attomoles (an attomole is 10 moles)) can be detected using the Tropix system in conjunction with the plate-reading luminometer.

(ii) Colorimetric Detection

Standard alkaline phosphatase colorimetric substrates are also suitable for the above detection reactions. Typically substrates include 4-nitrophenyl phosphate (Boehringer Mannheim). Results of colorimetric assays can be evaluated in multiwell plates (as above) using a plate-reading spectrophotometer (Molecular Devices, Menlo Park Calif.). The use of the light emission system is more sensitive than the colorimetric systems.

While the invention has been described with reference to specific methods and embodiments, it will be appreciated that various modifications and changes may be made without departing from the invention.

It is claimed:

1. A method of screening for molecules capable of binding to a selected test sequence in a duplex DNA, comprising
   (i) adding a molecule to be screened to a test system composed of (a) a DNA binding protein that is effective to bind to a screening sequence in a duplex DNA with a binding affinity that is substantially independent of such test sequence adjacent the screening sequence, but that is sensitive to binding of molecules to such test sequence, when the test sequence is adjacent the screening sequence, and (b) a duplex DNA having said screening and test sequences adjacent one another, where the binding protein is present in an amount that saturates the screening sequence in the duplex DNA,
   (ii) incubating the molecule in the test system for a period sufficient to permit binding of the molecule being tested to the test sequence in the duplex DNA, and
   (iii) comparing the amount of binding protein bound to the duplex DNA before and after said adding.

2. The method of claim 1, where the screening sequence/binding protein is selected from the group consisting of EBV origin of replication/EBNA, HSV origin of replication/UL9, VZV origin of replication-/UL9-like, and HPV origin of replication/E2, and lambda $o_L$-$o_R$/cro.

3. The method of claim 2, where the DNA screening sequence is from the HSV origin of replication and the binding protein is UL9.

4. The method of claim 3, wherein the DNA screening sequence is selected from the group consisting of SEQ ID NO:1, SEQ ID NO:2, and SEQ ID NO:15.

5. The method of claim 1, where said comparing is accomplished using either a gel band-shift assay or a filter-binding assay.

6. The method of claim 1, where said comparing includes the use of a capture system that traps DNA free of bound protein.

7. The method of claim 6, where the capture system involves the biotinylation of a nucleotide within the screening sequence (i) that does not eliminate the protein's ability to bind to the screening sequence, (ii) that is capable of binding streptavidin, and (iii) where the biotin moiety is protected from interactions with streptavidin when the protein is bound to the screening sequence.

8. A screening system for identifying molecules that are capable of binding to a test sequence in a target duplex DNA sequence, comprising
   a duplex DNA having screening and test sequences adjacent one another,
   a DNA binding protein that is effective to bind to said screening sequence in the duplex DNA with a binding affinity that is substantially independent of a test sequence adjacent the screening sequence, but which is sensitive to binding of molecules to such test sequence, when the test sequence is adjacent the screening sequence, and where the binding protein is present in an amount that saturates the screening sequence in the duplex DNA, and
   means for detecting the amount of binding protein bound to the DNA.

9. The system of claim 8, where the test sequences are selected from the group consisting of EBV origin of replication, HSV origin of replication, VZV origin of replication, HPV origin of replication, interleukin 2 enhancer, HIV-LTR, HBV enhancer, and fibrinogen promoter.

10. The system of claim 8, where the test sequences are selected from a group of randomly generated sequences.

11. The system of claim 8, where the screening sequence/binding protein is selected from the group consisting of EBV origin of replication/EBNA, HSV origin of replication/UL9, VZV origin of replication/UL9-like, and HPV origin of replication/E2, and lambda $o_L$-$o_R$/cro.

12. The system of claim 11, where the DNA screening sequence is from the HSV origin of replication and the binding protein is UL9.

13. The system of claim 12, wherein the DNA screening sequence is selected from the group consisting of SEQ ID NO:1, SEQ ID NO:2, and SEQ ID NO:15.

14. The system of claim 13, where the DNA screening sequence is SEQ ID NO1.

15. The system of claim 14, where the U residue in position 8 is biotinylated.

16. The system of claim 15, where said detection means includes streptavidin, and the streptavidin is bound to a solid support.

17. The system of claim 16, where streptavidin is used to capture the duplex DNA when it is free of bound protein.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 11 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: UL9 BINDING SITE, HSV oriS, higher affinity ( x i ) SEQUENCE DESCRIPTION: SEQ ID NO:1:

CGTTCGCACT T                     11

( 2 ) INFORMATION FOR SEQ ID NO:2:

( i ) SEQUENCE CHARACTERISTICS:
        ( A ) LENGTH: 11 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: UL9 BINDING SITE, HSV oriS, lower affinity ( x i ) SEQUENCE DESCRIPTION: SEQ ID NO:2:

TGCTCGCACT T                     11

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: UL9Z1 TEST SEQ. / UL9 ASSAY SEQ.

( x i ) SEQUENCE DESCRIPTION: SEQ ID NO:3:

GCGCGCGCGC GTTCGCACTT CCGCCGCCGG           30

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

-continued ( i i i ) HYPOTHETICAL: NO ( i v ) ANTI-SENSE: NO ( v i ) ORIGINAL SOURCE:
    ( C ) INDIVIDUAL ISOLATE: UL9Z2 TEST SEQ. / UL9 ASSAY SEQ.

( x i ) SEQUENCE DESCRIPTION: SEQ ID NO:4:

GGCGCCGGCC GTTCGCACTT CGCGCGCGCG     30

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: UL9 CCCG TEST SEQ. / UL9 ASSAY SEQ.

( x i ) SEQUENCE DESCRIPTION: SEQ ID NO:5:

GGCCCGCCCC GTTCGCACTT CCCGCCCCGG     30

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: UL9 GGGC TEST SEQ. / UL9 ASSAY SEQ.

( x i ) SEQUENCE DESCRIPTION: SEQ ID NO:6:

GGCGGGCGCC GTTCGCACTT GGGCGGGCGG     30

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: UL9 ATAT TEST SEQ. / UL9 ASSAY SEQ.

( x i ) SEQUENCE DESCRIPTION: SEQ ID NO:7:

GGATATATAC GTTCGCACTT TAATTATTGG     30

( 2 ) INFORMATION FOR SEQ ID NO:8:

( i ) SEQUENCE CHARACTERISTICS:

(A) LENGTH: 30 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: UL9 polyA TEST SEQ. / UL9 ASSAY SEQ.

(xi) SEQUENCE DESCRIPTION: SEQ ID NO:8:

GGAAAAAAAC GTTCGCACTT AAAAAAAAGG 30

(2) INFORMATION FOR SEQ ID NO:9:

(i) SEQUENCE CHARACTERISTICS:
(A) LENGTH: 30 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: UL9 polyT TEST SEQ. / UL9 ASSAY SEQ.

(xi) SEQUENCE DESCRIPTION: SEQ ID NO:9:

GGTTTTTTTC GTTCGCACTT TTTTTTTTGG 30

(2) INFORMATION FOR SEQ ID NO:10:

(i) SEQUENCE CHARACTERISTICS:
(A) LENGTH: 30 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: UL9 GCAC TEST SEQ. / UL9 ASSAY SEQ.

(xi) SEQUENCE DESCRIPTION: SEQ ID NO:10:

GGACGCACGC GTTCGCACTT GCAGCAGCGG 30

(2) INFORMATION FOR SEQ ID NO:11:

(i) SEQUENCE CHARACTERISTICS:
(A) LENGTH: 30 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: UL9 ATori-1 TEST SEQUENCE / UL9 ASSAY SEQ.

( x i ) SEQUENCE DESCRIPTION: SEQ ID NO:11:

GCGTATATAT CGTTCGCACT TCGTCCCAAT                                           30

( 2 ) INFORMATION FOR SEQ ID NO:12:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: oriECO2 TEST SEQ. / UL9 ASSAY SEQ.

( x i ) SEQUENCE DESCRIPTION: SEQ ID NO:12:

GGCGAATTCG ACGTTCGCAC TTCGTCCCAA T                                         31

( 2 ) INFORMATION FOR SEQ ID NO:13:

( i ) SEQUENCE CHARACTERISTICS:
        ( A ) LENGTH: 32 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: oriECO3 TEST SEQ. / UL9 ASSAY SEQ.

( x i ) SEQUENCE DESCRIPTION: SEQ ID NO:13:

GGCGAATTCG ATCGTTCGCA CTTCGTCCCA AT                                        32

( 2 ) INFORMATION FOR SEQ ID NO:14:

( i ) SEQUENCE CHARACTERISTICS:
        ( A ) LENGTH: 36 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: WILD TYPE ( x i ) SEQUENCE DESCRIPTION: SEQ ID NO:14:

AAGTGAGAAT TCGAAGCGTT CGCACTTCGT CCCAAT                                    36

( 2 ) INFORMATION FOR SEQ ID NO:15:

( i ) SEQUENCE CHARACTERISTICS:
        ( A ) LENGTH: 9 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO (iv) ANTI-SENSE: NO (vi) ORIGINAL SOURCE:
    (C) INDIVIDUAL ISOLATE: TRUNCATED UL9 BINDING SITE, COMPARE SEQ ID NO:1

(xi) SEQUENCE DESCRIPTION: SEQ ID NO:15:

TTCGCACTT    9

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: HSVB1/4, SEQUENCE OF COMPETITOR DNA MOLECULE (xi) SEQUENCE DESCRIPTION: SEQ ID NO:16:

GGTCGTTCGC ACTTCGC    17